US011952525B2

(12) United States Patent
Hayashi et al.

(10) Patent No.: US 11,952,525 B2
(45) Date of Patent: Apr. 9, 2024

(54) COMPOUND, COMPOSITION, LIQUID CRYSTAL COMPOSITION, AND DEVICE

(71) Applicant: DIC Corporation, Tokyo (JP)

(72) Inventors: Masanao Hayashi, Saitama (JP); Takaya Ikeuchi, Saitama (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 18/015,076

(22) PCT Filed: Jul. 29, 2021

(86) PCT No.: PCT/JP2021/028033

§ 371 (c)(1),
(2) Date: Jan. 9, 2023

(87) PCT Pub. No.: WO2022/030343

PCT Pub. Date: Feb. 10, 2022

(65) Prior Publication Data

US 2023/0313044 A1 Oct. 5, 2023

(30) Foreign Application Priority Data

Aug. 6, 2020 (JP) ................................ 2020-133716

(51) Int. Cl.
*C09K 19/32* (2006.01)
*C07C 25/18* (2006.01)
*C07C 25/24* (2006.01)

(52) U.S. Cl.
CPC .............. *C09K 19/32* (2013.01); *C07C 25/18* (2013.01); *C07C 25/24* (2013.01)

(58) Field of Classification Search
CPC ...................................................... C09K 19/32
See application file for complete search history.

(56) References Cited

U.S. PATENT DOCUMENTS

2018/0337445 A1 11/2018 Sullivan et al.

FOREIGN PATENT DOCUMENTS

| | | |
|---|---|---|
| JP | H11201703 | 7/1999 |
| JP | 2002128717 | 5/2002 |
| JP | 2013103897 | 5/2013 |
| JP | 2019509356 | 4/2019 |
| JP | 2019167537 | 10/2019 |

*Primary Examiner* — Chanceity N Robinson
(74) *Attorney, Agent, or Firm* — JCIPRNET

(57) ABSTRACT

A compound having large refractive index anisotropy (Δn), the effect of increasing the phase transition temperature of a liquid crystal phase, and high solubility, and showing large dielectric anisotropy (Δε) in a high frequency region, a composition containing the compound, a liquid crystal composition, and a device using the liquid crystal composition. The compound has large refractive index anisotropy Δn, sufficiently high $T_{n-i}$, and high compatibility with a liquid crystal composition, and shows large dielectric anisotropy in a high frequency region, and is thus useful for a material of an element of a device such as a high-frequency phase shifter, a phased array antenna, an image recognition device, a distance measuring device, a liquid crystal display device, a liquid crystal lens, a birefringent lens for stereoscopic image display.

16 Claims, No Drawings

COMPOUND, COMPOSITION, LIQUID CRYSTAL COMPOSITION, AND DEVICE

CROSS-REFERENCE TO RELATED APPLICATION

This application is a 371 application of the international PCT application serial no. PCT/JP2021/028033, filed on Jul. 29, 2021, which claims the priority benefit of Japan application no. 2020-133716, filed on Aug. 6, 2020. The entirety of each of the above-mentioned patent applications is hereby incorporated by reference herein and made a part of this specification.

TECHNICAL FIELD

The present invention relates to a compound, a composition containing the compound, a liquid crystal composition, and a device using an element using the liquid crystal composition.

BACKGROUND ART

Liquid crystal compositions are used for mobile terminals such as a smartphone, a tablet device, and the like, and display applications such as TV, a window display, and the like. An antenna which transmits/receives radio waves between a mobile body, such as a vehicle, and a communication satellite attracts attention as a novel application of liquid crystal compositions.

In general, satellite communication uses a parabolic antenna, but when used for a mobile body, the parabolic antenna is required to be directed in the satellite direction as needed, and thus a large mobile portion is required. However, an antenna using a liquid crystal composition can change the transmission/reception direction of radio waves by the motion of liquid crystal, and thus the antenna itself need not be moved, and the shape of the antenna can be made plane.

The refractive index anisotropy Δn of a liquid crystal composition required for these applications is, for example, about 0.4 and is very large as compared with Δn required for display applications. Also, for use for antennas, a liquid crystal phase is required to be maintained even at 100° C. or more, and thus a compound having a high phase transition temperature is required. Compounds having a tetralin (1,2,3,4-tetrahydronaphthalene) structure and a NCS group have been reported as compounds having large Δn (Patent Literatures 1 to 4). However, when added to a liquid crystal composition for antenna application, these compounds have the large effect of increasing the phase transition temperature, but the compounds have low solubility and thus have the problem of precipitation during storage for a long time. In addition, a compound having a fluorine group as a polar group is reported as a compound having a tetralin structure, but the compound has small dielectric anisotropy in a high frequency region and thus has insufficient phase modulation characteristic (Patent Literatures 5 and 6). Thus, there is demand for developing a compound having large Δn, the effect of increasing the phase transition temperature of a liquid crystal phase, and high solubility, and showing large dielectric anisotropy in a high frequency region.

CITATION LIST

Patent Literature

PTL 1: Specification of US Patent Application Publication No. 2018/0337445
PTL 2: Japanese Unexamined Patent Application Publication No. 2019-167537
PTL 3: Japanese Unexamined Patent Application Publication No. 2013-103897
PTL 4: Japanese Unexamined Patent Application Publication No. 2019-509356
PTL 5: Japanese Unexamined Patent Application Publication No. H11-201703
PTL 6: Japanese Unexamined Patent Application Publication No. 2002-128717

SUMMARY OF INVENTION

Technical Problem

A problem to be solved by the invention is to provide a compound having large refractive index anisotropy (Δn), the effect of increasing the phase transition temperature of a liquid crystal phase, and high solubility, and showing large dielectric anisotropy (Δε) in a high frequency region, and also provide a liquid crystal composition containing the compound and a device using an element using the liquid crystal composition.

Solution to Problem

As a result of earnest research for solving the problem, the inventors led to the development of a specific compound. That is, the present invention provides a compound represented by general formula (I) below,

[Chem. 1]

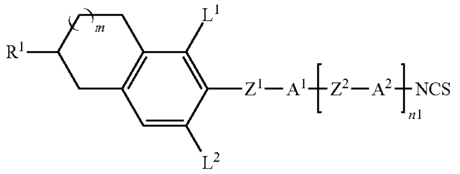

(I)

(in the formula, $R^1$ represents a hydrogen atom, a linear alkyl group having 1 to 20 carbon atoms, or a branched or cyclic alkyl group having 3 to 20 carbon atoms, any hydrogen atom in the alkyl group may be substituted by a halogen atom, one or two or more $-CH_2-$ in the alkyl group may be each independently substituted by $-O-$, $-S-$, $-CO-$, $-CS-$, $-COO-$, $-OCO-$, $-CO-S-$, $-S-CO-$, $-O-CO-O-$, $-CO-NH-$, $-NH-CO-$, $-CH{=}CH-$, $-CF{=}CF-$, or $-C{\equiv}C-$, but oxygen atoms are not directly bonded to each other, $A^1$ and $A^2$ each independently represent a hydrocarbon ring or hetero ring having 3 to 16 carbon atoms, which may be substituted, when a plurality of $A^2$ are present, they may be the same or different, $L^1$ and $L^2$ each independently represent a hydrogen atom, a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear alkyl group having 1 to 20 carbon atoms or a branched or cyclic alkyl group having 3 to 20 carbon atoms, in which one $—CH_2—$ or two or more $—CH_2—$ may be each independently substituted by —O—, —S—, —CO—, —CS—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, oxygen atoms are not directly bonded to each other, any hydrogen atom in the alkyl group may be substituted by a fluorine atom, $Z^1$ and $Z^2$ each independently represent a single bond, —CH═CH—, —CF═CF—, —C≡C—, —COO—, —OCO—, —OCOO—, $—CH_2O—$, $—OCH_2—$, $—CF_2O—$, $—OCF_2—$, —CH═CHCOO—, —OCOCH═CH—, $—CH═C(CH_3)COO—$, $—OCOC(CH_3)═CH—$, $—CH_2—CH(CH_3)COO—$, $—OCOCH(CH_3)—CH_2—$, $—OCH_2CH_2O—$, —CH═N—N═CH—, —CH═N—, —N═CH—, —N═N—, or an alkylene group having 1 to 20 carbon atoms, one or two or more $—CH_2—$ in the alkylene group may be each independently substituted by —O—, —COO—, or —OCO—, but oxygen atoms are not directly bonded to each other, when a plurality of $Z^2$ are present, they may be the same or different, m represents 0 or 1, and n1 represents an integer of 0 to 3).

The present invention also provides a composition containing the compound, a liquid crystal composition, and a device using an element using the liquid crystal composition.

Advantageous Effects of Invention

The compound of the present invention has large refractive index anisotropy Δn, the effect of increasing the phase transition temperature of a liquid crystal phase, and high solubility, and shows large dielectric anisotropy (Δε) in a high frequency region, and is thus useful for a material of an element of a device such as a high-frequency phase shifter, a phased array antenna, an image recognition device, a distance measuring device, a liquid crystal display device, a liquid crystal lens, a birefringent lens for stereoscopic image display, or the like.

DESCRIPTION OF EMBODIMENTS

The present invention provides a compound represented by general formula (I), a composition containing the compound, a liquid crystal composition, and a device using an element using the liquid crystal composition.

In the general formula (I), $R^1$ represents a hydrogen atom, a linear alkyl group having 1 to 20 carbon atoms, or a branched or cyclic alkyl group having 3 to 20 carbon atoms, any hydrogen atom in the alkyl group may be substituted by a halogen atom, and one or two or more $—CH_2—$ in the alkyl group may be each independently substituted by —O—, —S—, —CO—, —CS—, —COO—, —OCO—, —CO—S—, —S—CO—, —O—CO—O—, —CO—NH—, —NH—CO—, —CH═CH—, —CF═CF—, or —C≡C—, but oxygen atoms are not directly bonded to each other. From the viewpoint of compatibility with a liquid crystal composition, refractive index anisotropy, voltage retention rate, ease of synthesis, and availability of raw materials, $R^1$ preferably represents a hydrogen atom or a linear or branched alkyl group having 1 to 20 carbon atoms, in which any hydrogen atom in the group may be substituted by a halogen atom, and one or two or more $—CH_2—$ in the group may be each independently substituted by —O—, —S—, —CH═CH—, —CF═CF—, or —C≡C—, $R^1$ more preferably represents a linear or branched alkyl group having 1 to 12 carbon atoms, in which any hydrogen atom in the group may be substituted by a fluorine atom, and one or two or more $—CH_2—$ in the group may be each independently substituted by —O—, —CH═CH—, or —C≡C—, $R^1$ still more preferably represents an alkyl group having 1 to 8 carbon atoms, an alkoxy group having 1 to 7 carbon atoms, an alkenyl group having 2 to 8 carbon atoms, an alkenyloxy group having 1 to 7 carbon atom, or an alkynyl group having 2 to 8 carbon atoms, and $R^1$ particularly preferably represents an alkyl group having 2 to 5 carbon atoms, an alkoxy group having 1 to 4 carbon atoms, an alkenyl group having 2 to 5 carbon atoms, or an alkynyl group having 3 to 7 carbon atoms.

In the general formula (I), $A^1$ and $A^2$ each independently represent a hydrocarbon ring or hetero ring having 3 to 16 carbon atoms, which may be substituted, but when a plurality of $A^2$ are present, they may be the same or different. From the viewpoint of compatibility with a liquid crystal composition, refractive index anisotropy, dielectric anisotropy, voltage retention rate, ease of synthesis, and availability of raw materials, $A^1$ and $A^2$ may be each independently unsubstituted or substituted by one or more substituents $L^3$. When a plurality of substituents $L^3$ are present, they may be the same or different.

$A^1$ and $A^2$ preferably each represent a group which may be unsubstituted or substituted by one or more substituents $L^3$ and is selected from the group consisting of:

(a) a 1,4-cyclyhexylene group (one $—CH_2—$ or two or more nonadjacent $—CH_2—$ present in the group may be substituted by —O— or —S—);

(b) a 1,4-phenylene group (one —CH═ or two or more nonadjacent —CH═ present in the group may be substituted by —N═);

(c) a 1,4-cyclohexenylene group, a bicyclo[2.2.2]octane-1,4-diyl group, a naphthalene-2,6-diyl group, a naphthalene-1,4-diyl group, a 1,2,3,4-tetrahydronaphthalene-2,6-diyl group, a 5,6,7,8-tetrahydronaphthalene-1,4-diyl group, a decahydronaphthalene-2,6-diyl group, an anthracene-2,6-diyl group, an anthracene-1,4-diyl group, an anthracene-9,10-diyl group, and a phenanthrene-2,7-diyl group (a hydrogen atom present in each of these groups may be substituted by a fluorine atom or a chlorine atom, and one —CH═ or two or more-CH═ present in a naphthalene-2,6-diyl group, a naphthalene-1,4-diyl group, a 1,2,3,4-tetrahydronaphthalene-2,6-diyl group, a 5,6,7,8-tetrahydronaphthalene-1,4-diyl group, an anthracene-2,6-diyl group, an anthracene-1,4-diyl group, an anthracene-9,10-diyl group, or a phenanthrene-2,7-diyl group may be substituted by —N═); and (d) a thiophene-2,5-diyl group, a benzothiophene-2,5-diyl group, a benzothiophene-2,6-diyl group, a dibenzothiophene-3,7-diyl group, a dibenzothiophene-2,6-diyl group, and a thieno[3,2-b]thiophene-2,5-diyl group (one —CH═ or two or more nonadjacent —CH═ present in each of these groups may be substituted by —N═), and when a plurality of $A^2$ are present, they may be the same or different, and when a plurality of substituents $L^3$ are present, they may be the same or different. In addition, $A^1$ and $A^2$ more preferably each represent a group which may be unsubstituted or substituted by one or more substituents $L^3$ and is selected from a 1,4-phenylene group, a naphthalene-2,6-diyl group, a naphthalene-1,4-diyl group, a 5,6,7,8-tetrahydronaphthalene-1,4-diyl group, a phenanthrene-2,7-diyl group, a benzothiophene-2,5-diyl group, a benzothiophene-2,6-diyl group, a benzothiazole-2,5-diyl group, a benzothiazole-2,6-diyl group, a dibenzothiophene-3,7-diyl group, a dibenzothiophene-2,6-diyl group, and a thieno[3,2-b]thiophene-2,5-diyl group, and when a plurality of $A^2$ are present, they may be the same or different, and when a plurality of substituents $L^3$ are present, they may be the same or different. In addition, $A^1$ and $A^2$ each independently still more preferably represent a group selected from formula (A-1) to formula (A-17) below,

[Chem. 2]

(A-1)

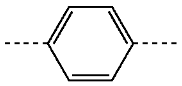

(A-2)

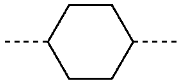

(A-3)

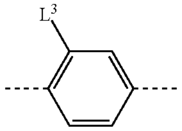

(A-4)

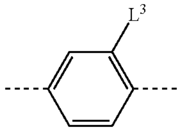

(A-5)

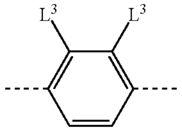

(A-6)

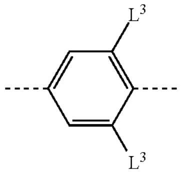

(A-7)

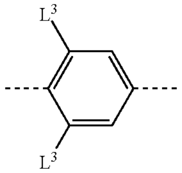

(A-8)

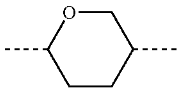

-continued (A-9)

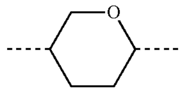

(A-10)

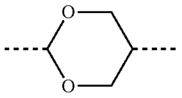

(A-11)

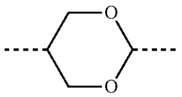

(A-12)

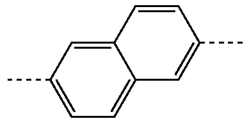

(A-13)

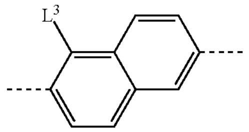

(A-14)

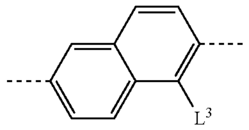

(A-15)

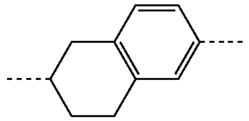

(A-16)

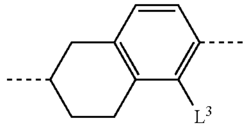

(A-17)

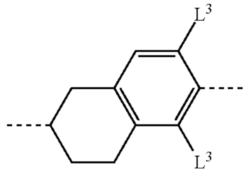

(in the formulae, a broken line represents a bond position, and when a plurality of $L^3$ are present, they may be the same or different), when a plurality of $A^2$ are present, they may be the same or different, and when a plurality of substituents $L^3$ are present, they may be the same or different, and $A^1$ and $A^2$ each independently even still more preferably represent a group selected from the formula (A-1) to the formula (A-7), the formula (A-12), the formula (A-15), and the formula (A-17) and particularly preferably represent a group selected from the formula (A-1) and the formula (A-3) to the formula (A-7).

$L^1$ and $L^2$ each independently represent a hydrogen atom, a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear alkyl group having 1 to 20 carbon atoms or a branched or cyclic alkyl group having 3 to 20 carbon atoms, in which one —$CH_2$— or two or more —$CH_2$— may be each independently substituted by —O—, —S—, —CO—, —CS—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, oxygen atoms are not directly bonded to each other, and any hydrogen atom in the alkyl group may be substituted by a fluorine atom. From the viewpoint of compatibility with a liquid crystal composition, refractive index anisotropy, dielectric anisotropy, voltage retention rate, ease of synthesis, and availability of raw materials, $L^1$ and $L^2$ each independently preferably represent a hydrogen atom, a fluorine atom, a chlorine atom, or a linear alkyl group having 1 to 20 carbon atoms or a branched or cyclic alkyl group having 3 to 20 carbon atoms, in which any hydrogen atom in the group may be substituted by a fluorine atom, and one —$CH_2$— or two or more —$CH_2$— in the group may be each independently substituted by —O—, —S—, —CH═CH—, —CF≡CF—, or —C≡C—, $L^1$ and $L^2$ each independently more preferably represent a hydrogen atom, a fluorine atom, or a linear alkyl group having 1 to 10 carbon atoms or a branched or cyclic alkyl group having 3 to 10 carbon atoms, in which any hydrogen atom in the group may be substituted by a fluorine atom, and one —$CH_2$— or two or more —$CH_2$— in the group may be each independently substituted by —O—, $L^1$ and $L^2$ each independently still more preferably represent a hydrogen atom, a fluorine atom, or a linear alkyl group having 1 to 10 carbon atoms or a branched or cyclic alkyl group having 3 to 10 carbon atoms, and $L^1$ and $L^2$ each independently particularly preferably represent a hydrogen atom, a fluorine atom, or a linear alkyl group having 1 to 8 carbon atoms.

$L^3$ each independently represent a hydrogen atom, a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear alkyl group having 1 to 20 carbon atoms or a branched or cyclic alkyl group having 3 to 20 carbon atoms, in which one —$CH_2$— or two or more —$CH_2$— may be each independently substituted by —O—, —S—, —CO—, —CS—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, oxygen atoms are not directly bonded to each other, and any hydrogen atom in the alkyl group may be substituted by a fluorine atom. From the viewpoint of compatibility with a liquid crystal composition, refractive index anisotropy, dielectric anisotropy, voltage retention rate, ease of synthesis, and availability of raw materials, $L^3$ each independently preferably represent a hydrogen atom, a fluorine atom, a chlorine atom, or a linear alkyl group having 1 to 20 carbon atoms or a branched or cyclic alkyl group having 3 to 20 carbon atoms, in which any hydrogen atom in the group may be substituted by a fluorine atom, and one —$CH_2$— or two or more —$CH_2$— in the group may be each independently substituted by —O—, —S—, —CH═CH—, —CF═CF—, or —C≡C—, $L^3$ each independently more preferably represent a hydrogen atom, a fluorine atom, or a linear alkyl group having 1 to 10 carbon atoms or a branched or cyclic alkyl group having 3 to 10 carbon atoms, in which any hydrogen atom in the group may be substituted by a fluorine atom, and —$CH_2$— in the group may be substituted by —O—, $L^3$ each independently still more preferably represent a hydrogen atom, a fluorine atom, or a linear alkyl group having 1 to 10 carbon atoms or a branched or cyclic alkyl group having 3 to 10 carbon atoms, and $L^3$ each independently particularly preferably represent a hydrogen atom, a fluorine atom, or a linear alkyl group having 1 to 8 carbon atoms.

In the general formula (I), $Z^1$ and $Z^2$ each independently represent a single bond, —CH═CH—, —CF═CF—, —C≡C—, —COO—, —OCO—, —OCOO—, —$CH_2O$—, —$OCH_2$—, —$CF_2O$—, —$OCF_2$—, —CH═CHCOO—, —OCOCH═CH—, —CH═C($CH_3$)COO—, —OCOC($CH_3$)═CH—, —$CH_2$—CH($CH_3$)COO—, —OCOCH($CH_3$)—$CH_2$—, —$OCH_2CH_2O$—, —CH═N—N═CH—, —CH═N—, —N═CH—, —N═N—, or an alkylene group having 1 to 20 carbon atoms, one —$CH_2$— or two or more —$CH_2$— in the alkylene group may be each independently substituted by —O—, —COO—, or —OCO—, but oxygen atoms are not directly bonded to each other. When a plurality of $Z^2$ are present, they may be the same or different. $Z^1$ and $Z^2$ each independently preferably represent a single bond, —CH═CH—, —CF═CF—, —C≡C—, —COO—, —OCO—, —OCOO—, —CH═CHCOO—, —OCOCH═CH—, —CH═C($CH_3$)COO—, —OCOC($CH_3$)═CH—, —CH═N—N═CH—, —N═N—, —CH═N—, or —N═CH—, $Z^1$ and $Z^2$ each independently more preferably represent a single bond, —CH═CH—, —CF═CF—, —C≡C—, —COO—, —OCO—, —CH═N—N═CH—, —N═N—, —CH═N—, or —N═CH—, and particularly preferably represent a single bond, —CH═CH—, —CF═CF—, —C≡C—, —CH═N—N═CH—, —CH═N—, or —N═CH—. In view of refractive index anisotropy and low viscosity, $Z^1$ and $Z^2$ each independently most preferably represent a single bond or —C≡C—.

In addition, from the viewpoint of high refractive index anisotropy, at least one of $Z^1$ and $Z^2$ preferably represents —C≡C—.

In the general formula (I), n1 represents an integer of 0 or 1 to 3, but from the viewpoint of compatibility with a liquid crystal composition, phase transition point, refractive index anisotropy, dielectric anisotropy, voltage retention rate, ease of synthesis, and availability of raw materials, n1 preferably represents an integer of 0, 1, or 2, and particularly preferably represents an integer of 0 or 1.

In the general formula (I), m preferably represents an integer of 0 or 1 and particularly preferably represents 1.

The compound represented by the general formula (I) has 2 or more ring structures (monoring or fused ring) in the structure thereof. In particular, when ring structures are joined to each other to form a rod-shaped molecular structure in the whole compound, the phase transition point is increased due to improvement in crystallinity, and thus the liquid crystal phase temperature can be significantly increased when added to a liquid crystal composition. Further, the compound represented by the general formula (I) has a tetralin structure or an indane structure, and thus has high rigidity over the whole molecule while weakening the intermolecular interaction in a composition, and the liquid crystal phase temperature range can be effectively widened while maintaining compatibility. Further, the bonding to each other of at least one pair of rings through linking group —C≡C— indicates the excellent effect of effectively increasing Δn by conjugating and widening π electrons in the ring structures over the while compound and showing large dielectric anisotropy in a high-frequency region because the compound has a thioisocyanate group (-NCS group) at a terminal. In particular, a thioisocyanate group has small rotational viscosity ($\gamma_1$) and is advantageous in terms of response speed as compared with a cyano group which is a similar polar group.

In addition, from the viewpoint of stability of the compound, oxygen atoms and/or an oxygen atom and a sulfur atom in the general formula (I) are preferably not directly bonded to each other.

From the viewpoint of a wide temperature range showing a liquid crystal phase, compatibility with a liquid crystal composition, refractive index anisotropy, dielectric anisotropy, voltage retention rate, ease of synthesis, and availability of raw materials, the compound represented by the general formula (I) is more preferably a compound represented by general formula (I-i) below:

[Chem. 3]

(I-i)

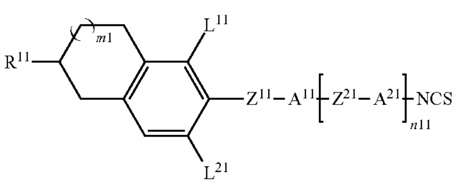

(In the formula, $R^{11}$ represents a hydrogen atom or a linear or branched alkyl group having 1 to 20 carbon atoms.

any hydrogen atom in the alkyl group may be substituted by a halogen atom, one or two or more —$CH_2$— in the alkyl group may be each independently substituted by —O—, —S—, —CH=CH—, —CF≡CF—, or $A^{11}$ and $A^{21}$ each independently represent a 1,4-phenylene group, a naphthalene-2,6-diyl group, a naphthalene-1,4-diyl group, a 5,6,7,8-tetrahydronaphthalene-1,4-diyl group, a phenanthrene-2,7-diyl group, a benzothiophene-2,5-diyl group, a benzothiophene-2,6-diyl group, a benzothiazole-2,5-diyl group, a benzothiazole-2,6-diyl group, a dibenzothiophene-3,7-diyl group, a dibenzothiophene-2,6-diyl group, or a thieno[3,2-b]thiophene-2,5-diyl group, when a plurality of $A^{21}$ are present, they may be the same or different, these groups may be unsubstituted or substituted by one or more substituents $L^{31}$, $L^{11}$ and $L^{21}$ each independently represent a hydrogen atom, a fluorine atom, a chlorine atom, or a linear alkyl group having 1 to 20 carbon atoms or a branched or cyclic alkyl group having 3 to 20 carbon atoms, any hydrogen atom in the alkyl group may be substituted by a fluorine atom, one —$CH_2$— or two or more —$CH_2$— in the alkyl group may be each independently substituted by —O—, —S—, —CH=CH—, —CF≡CF—, or $L^{31}$ each independently represent a fluorine atom, a chlorine atom, or a linear alkyl group having 1 to 20 carbon atoms or a branched or cyclic alkyl group having 3 to 20 carbon atoms, any hydrogen atom in the alkyl group may be substituted by a fluorine atom, one —$CH_2$— or two or more —$CH_2$— in the alkyl group may be each independently substituted by —O—, —S—, —CH=CH—, —CF≡CF—, or when a plurality of $L^{31}$ are present, they may be the same or different, $Z^{11}$ and $Z^{21}$ each independently represent —$OCH_2$—, —$CH_2O$—, —$CH_2CH_2$—, —$CF_2O$—, —$OCF_2$—, —CH=CH—, —N=N—, —CH=N—, —N=CH—, —N=N—, —CH=N—N=CH—, —CF≡CF—, or single bond, when a plurality of $Z^{21}$ are present, they may be the same or different, at least one of $Z^{11}$ and $Z^{21}$ present in the formula represents m1 represents 0 or 1, and n11 represents an integer of 0 to 3); and the compound is still more preferably a compound represented by general formula (I-ii) below:

[Chem. 4]

(I-ii)

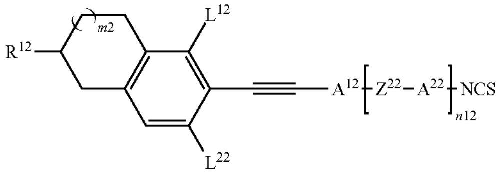

(In the formula, $R^{12}$ represents a linear or branched alkyl group having 1 to 12 carbon atoms, any hydrogen atom in the alkyl group may be substituted by a fluorine atom, one or two or more —$CH_2$— in the alkyl group may be each independently substituted by —O—, —CH=CH—, or —C≡C—, $A^{12}$ and $A^{22}$ each independently represent a group selected from formula (A-ii-1) to formula (A-ii-17) below,

[Chem. 5]

(A-ii-1)

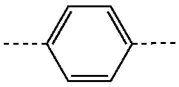

(A-ii-2)

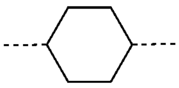

(A-ii-3)

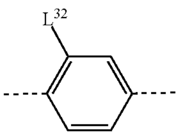

(A-ii-4)

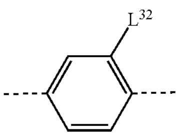

-continued (A-ii-5)

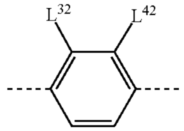

(A-ii-6)

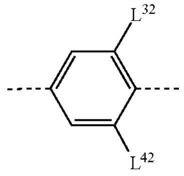

(A-ii-7)

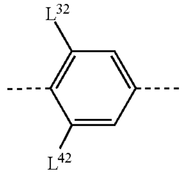

(A-ii-8)

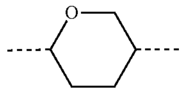

(A-ii-9)

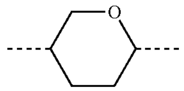

(A-ii-10)

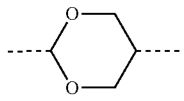

(A-ii-11)

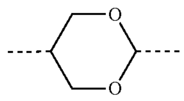

(A-ii-12)

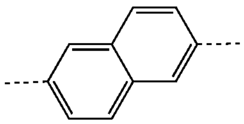

(A-ii-13)

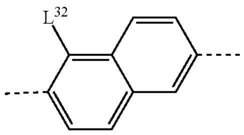

(A-ii-14)

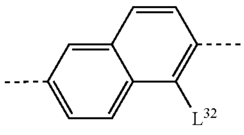

(A-ii-15)

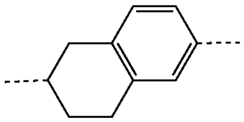

-continued (A-ii-16)

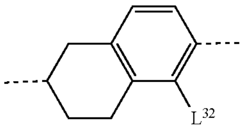

(A-ii-17)

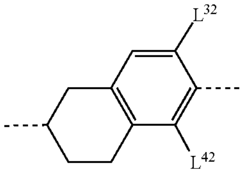

(in the formulae, a broken line represents a bond position, and when a plurality of each of $L^{32}$ and $L^{42}$ are present, they may be the same or different), when a plurality of $A^{22}$ are present, they may be the same or different, $L^{12}$, $L^{22}$, $L^{32}$, and $L^{42}$ each independently represent a hydrogen atom, a fluorine atom, or a linear alkyl group having 1 to 10 carbon atoms or a branched or cyclic alkyl group having 3 to 10 carbon atoms, any hydrogen atom in the alkyl group may be substituted by a fluorine atom, $-CH_2-$ in the alkyl group may be substituted by $-O-$, $Z^{22}$ each independently represent $-CH{=}CH-$, $-N{=}N-$, $-CH{=}N-$, $-N{=}CH-$, $-N{=}N-$, $-CH{=}N-N{=}CH-$, $-CF{=}CF-$, $-C{\equiv}C-$, or single bond, when a plurality of $Z^{22}$ are present, they may be the same or different, m2 represents 0 or 1, and n12 represents an integer of 0 or 1 to 3).

Among compounds represented by the general formula (I), structures of preferred compounds are represented by (I-iii) to (I-xviii).

[Chem. 6]

(I-iii)

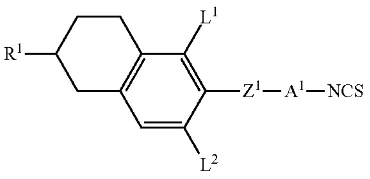

(I-iv)

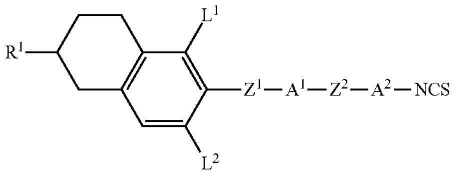

(I-v)

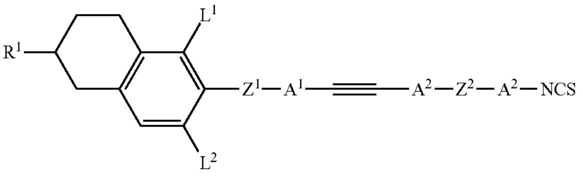

-continued (I-vi)

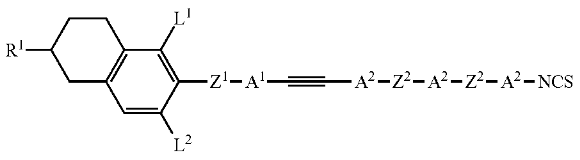

[Chem. 7]

(I-vii)

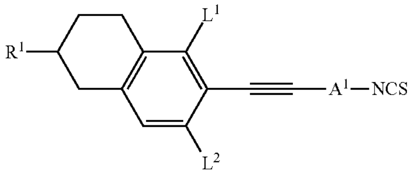

(I-viii)

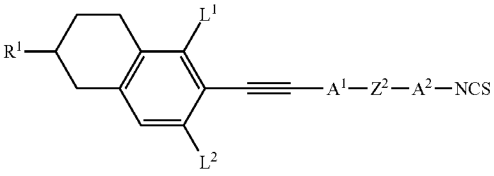

(I-ix)

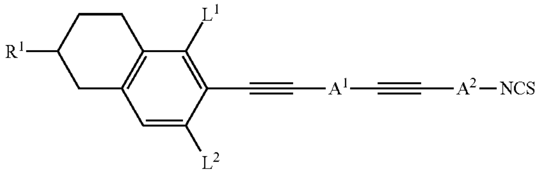

(I-x)

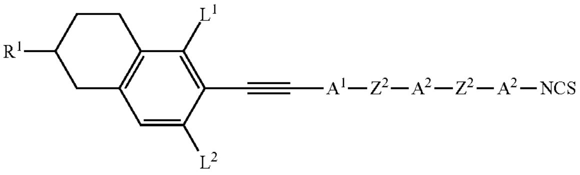

(I-xi)

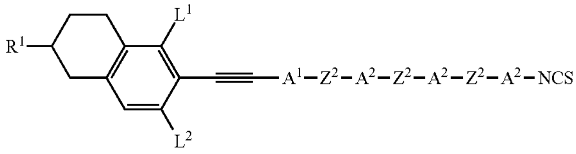

[Chem. 8]

(I-xii)

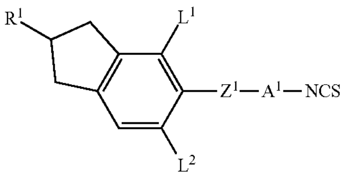

(I-xiii)

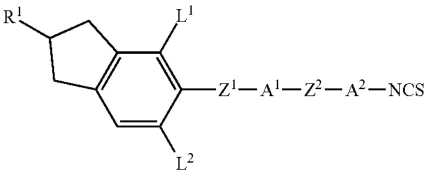

-continued (I-xiv)

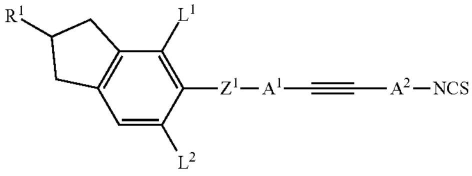

(I-xv)

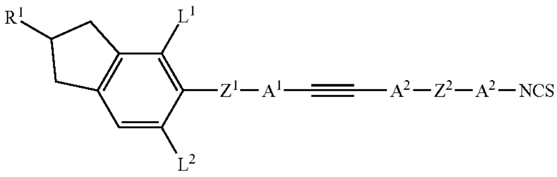

[Chem. 9]

(I-xvi)

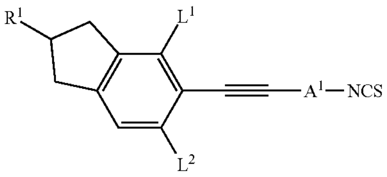

(I-xvii)

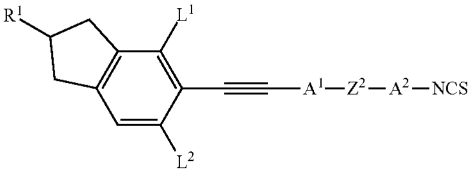

(I-xviii)

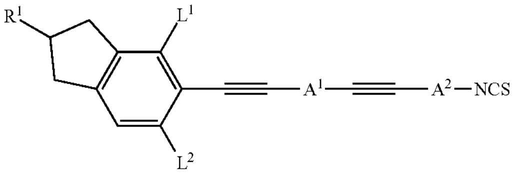

(In the formulae, $R^1$, $A^1$, $A^2$, $L^1$, $L^2$, $Z^1$, and $Z^2$ represent the same meanings as $R^1$, $A^1$, $A^2$, $L^1$, $L^2$, $Z^1$, and $Z^2$ in the general formula (I), and when in the formulae, a plurality of each of $A^2$ and $Z^2$ are present, they may be the same or different.)

More specific compounds of the compound (including more specific concepts) represented by the general formula (I) are represented by formula (I-1) to formula (I-67) below.

[Chem. 10]
(I-1)
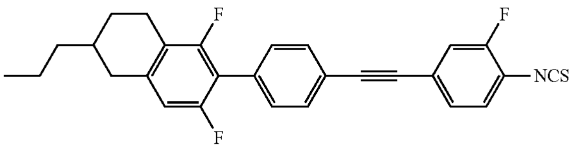
(I-2)
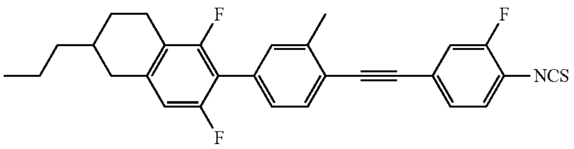
(I-3)
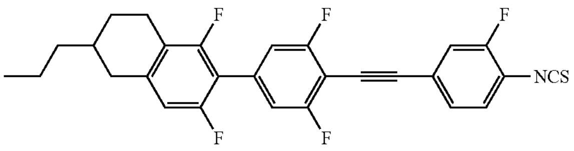
(I-4)
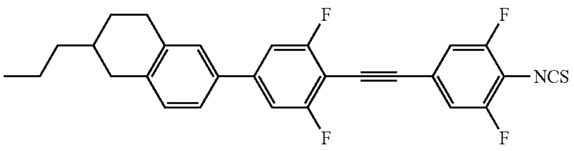
(I-5)
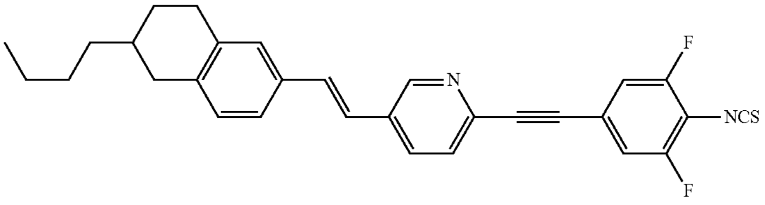
[Chem. 11]
(I-6)
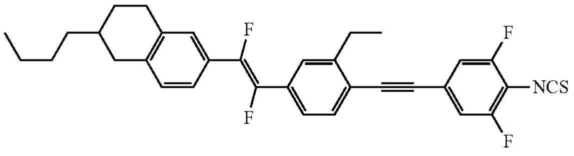
(I-7)
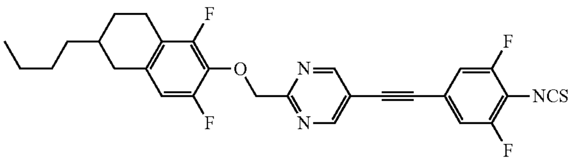
(I-8)
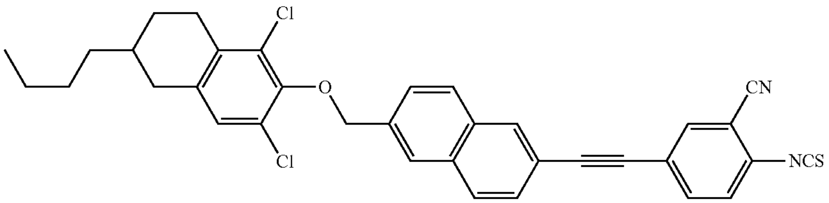
(I-9)
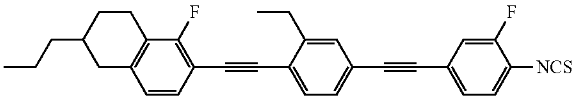
(I-10)
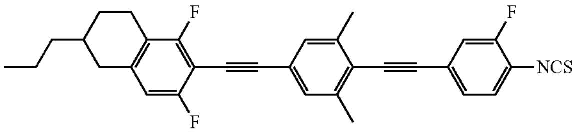
[Chem. 12]
(I-11)
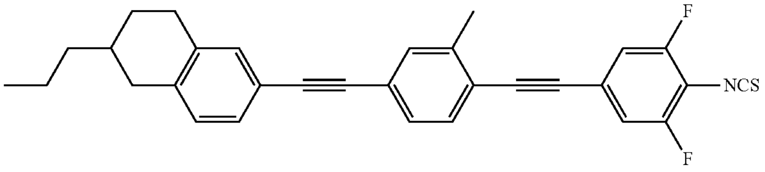
(I-12)
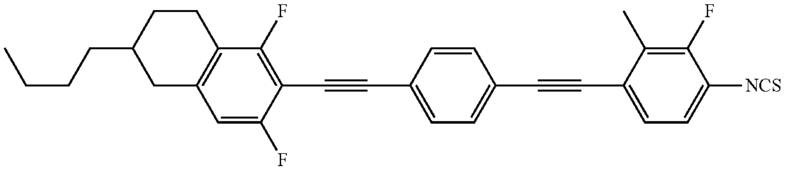

-continued
(I-13)
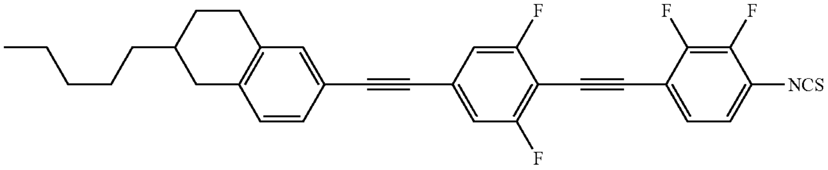
(I-14)
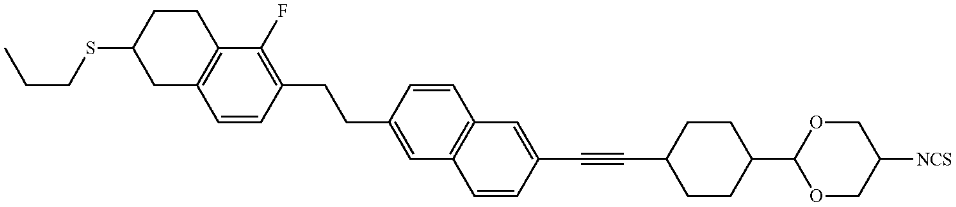
(I-15)
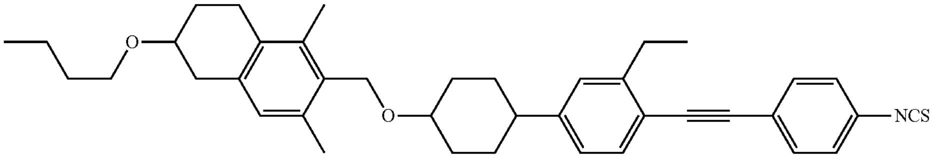
[Chem. 13]
(I-16)
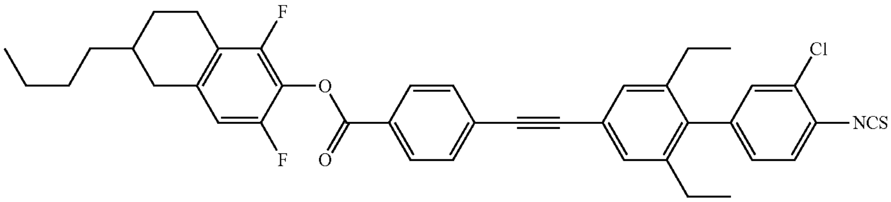
(I-17)
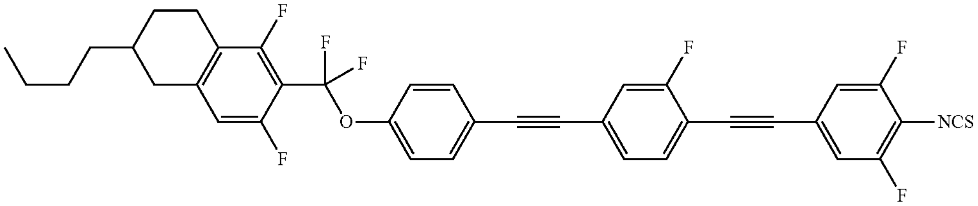
(I-18)
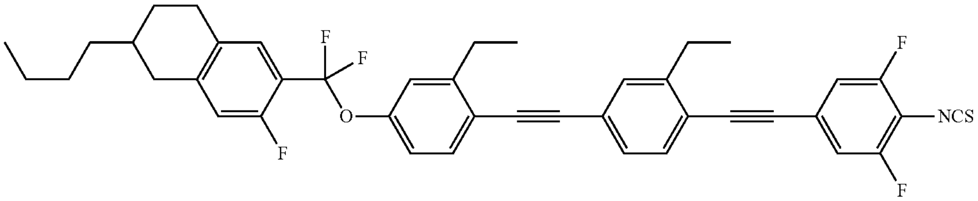
(I-19)
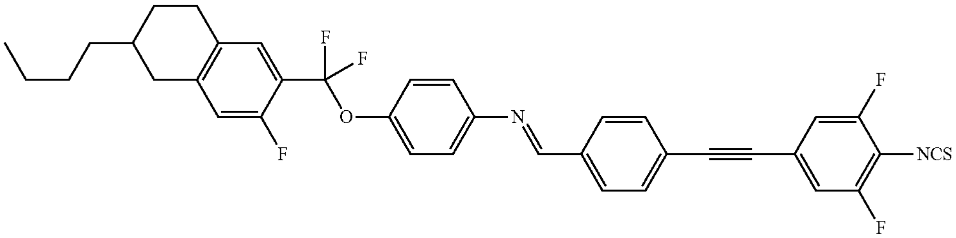

-continued
[Chem. 14]
(I-20)
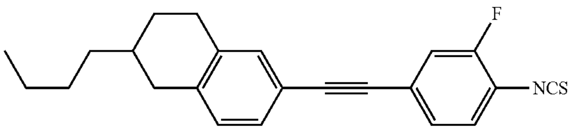
(I-21)
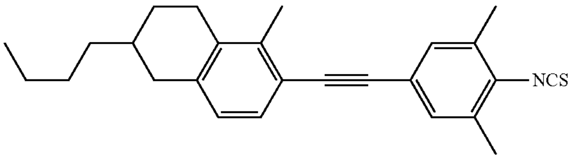
(I-22)
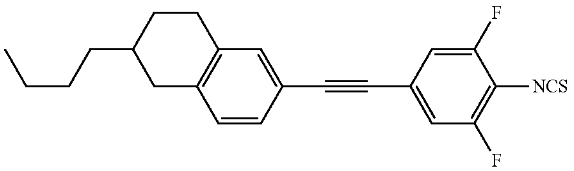
(I-23)
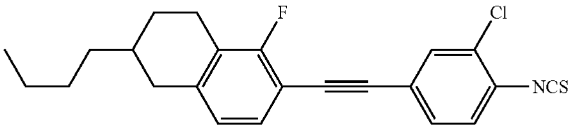
(I-24)
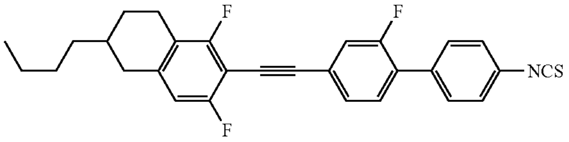
(I-25)
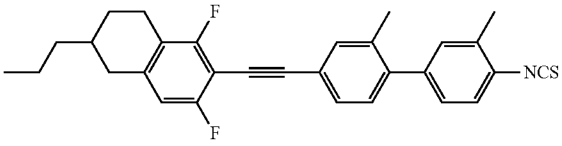
[Chem. 15]
(I-26)
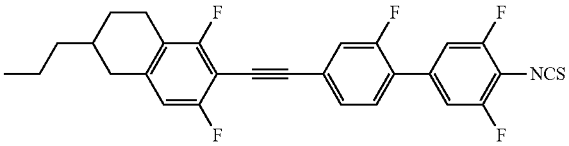
(I-27)
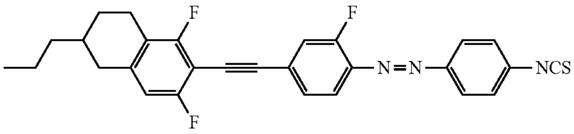
(I-28)
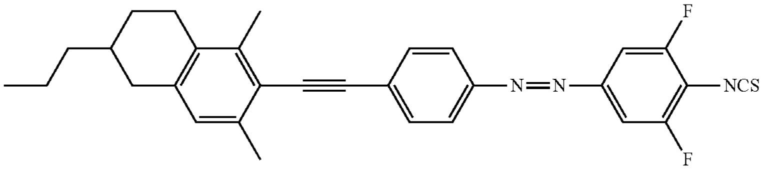
(I-29)
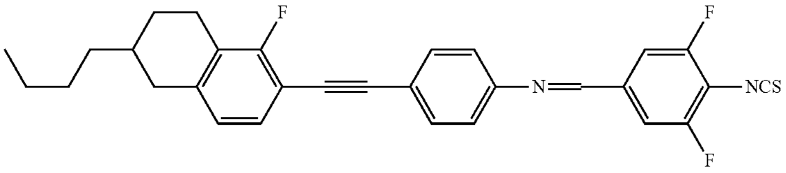
(I-30)
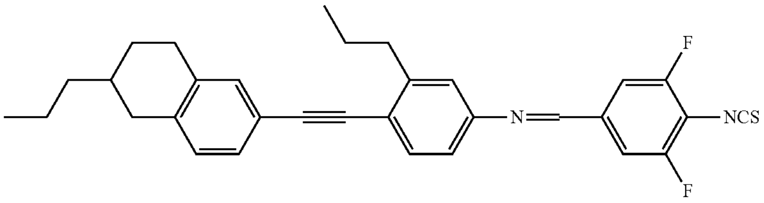
[Chem. 16]
(I-31)
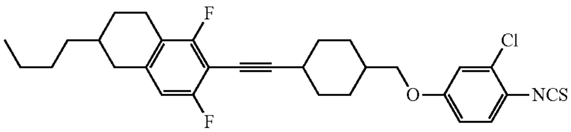
(I-32)
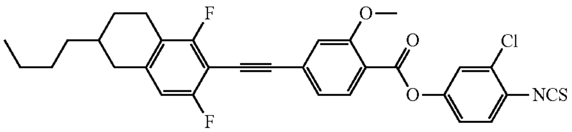

-continued
(I-33)
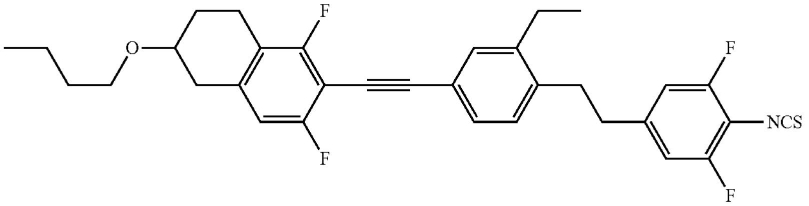
(I-34)
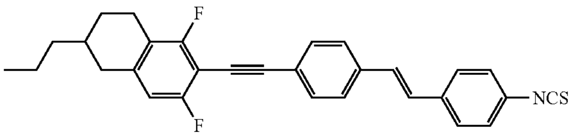
(I-35)
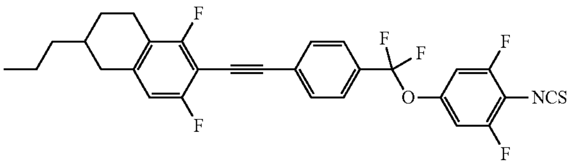
[Chem. 17]
(I-36)
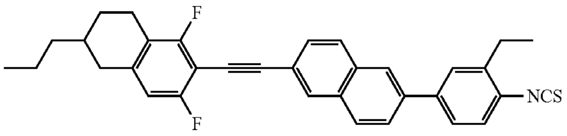
(I-37)
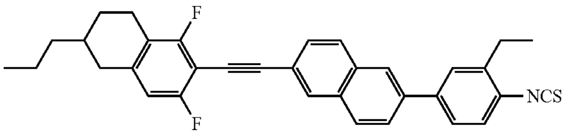
(I-38)
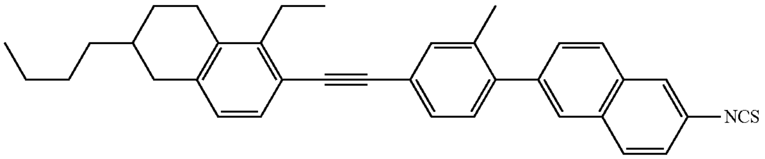
(I-39)
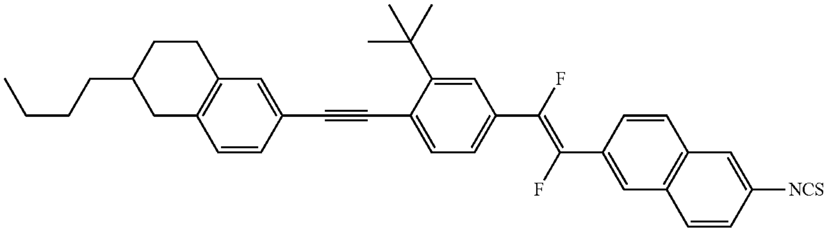
(I-40)
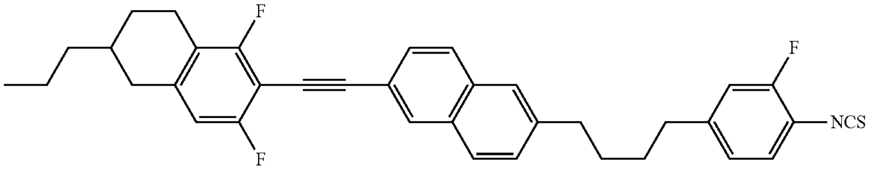
[Chem. 18]
(I-41)
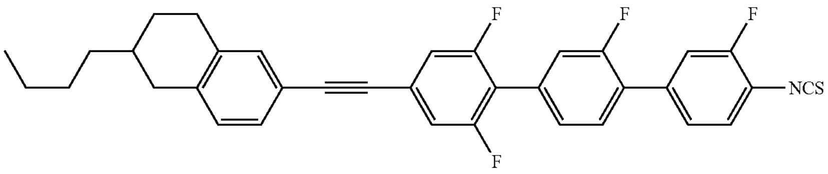
(I-42)
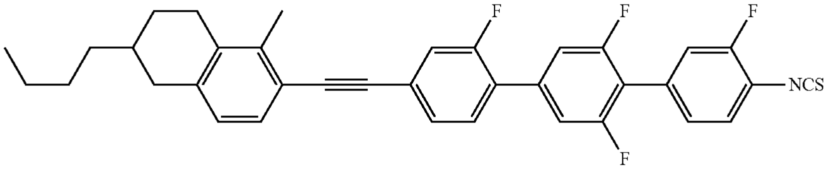

-continued
(I-43)
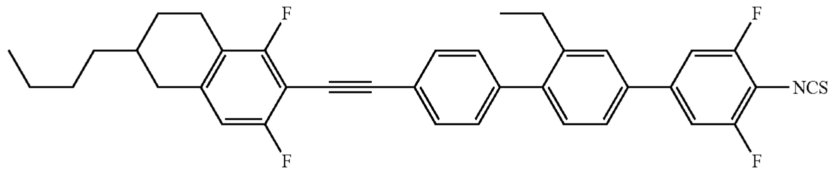
(I-44)
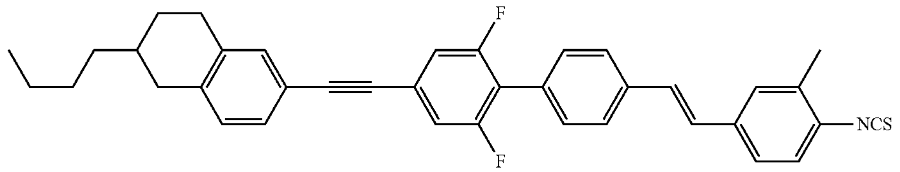
(I-45)
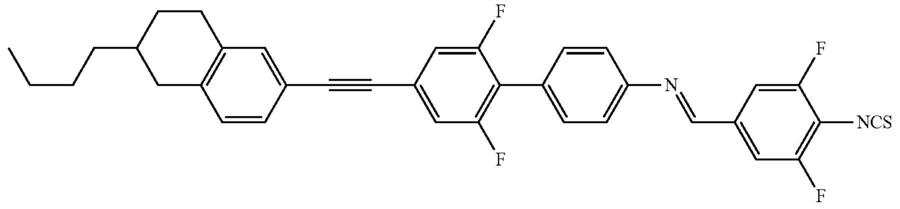
[Chem. 19]
(I-46)
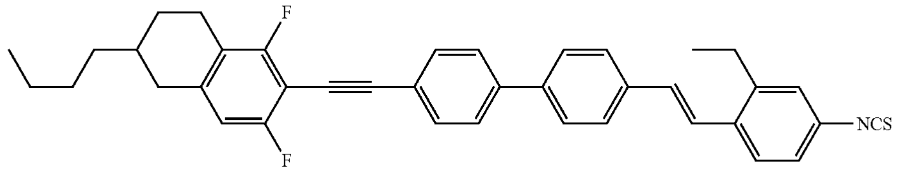
(I-47)
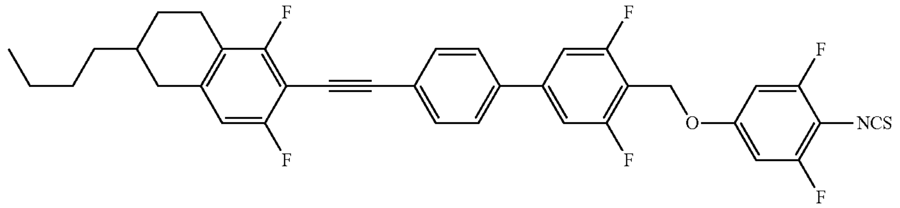
(I-48)
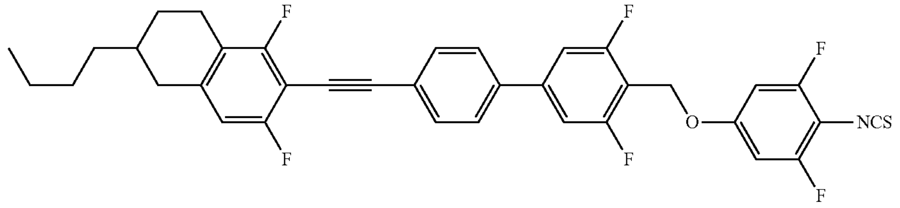
(I-49)
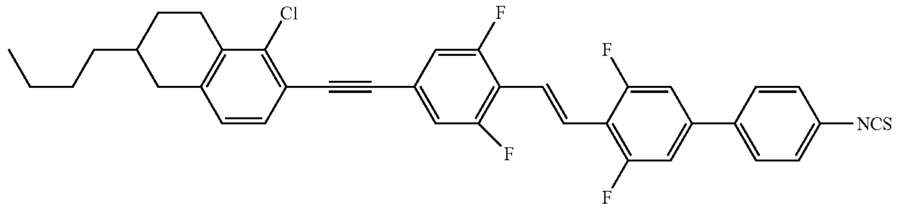

-continued
(I-50)
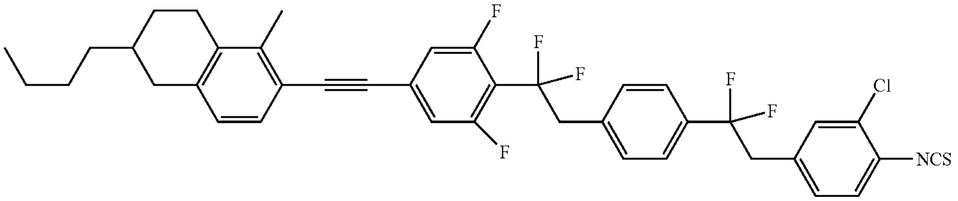
[Chem. 20]
(I-51)
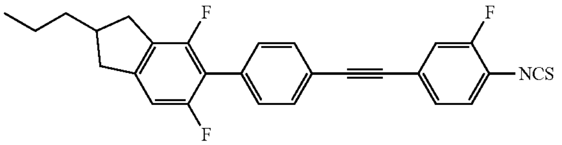
(I-52)
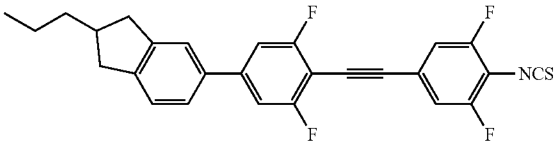
(I-53)
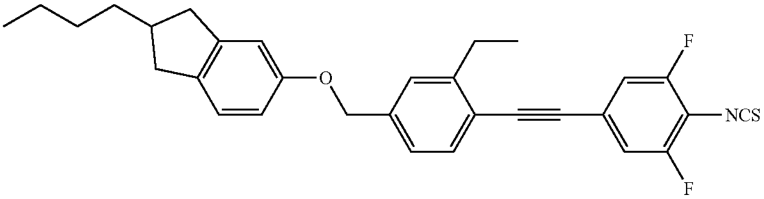
(I-54)
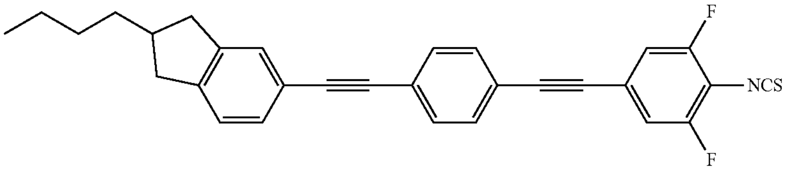
[Chem. 21]
(I-55)
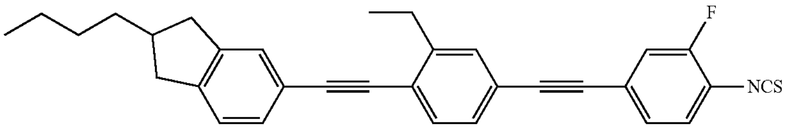
(I-56)
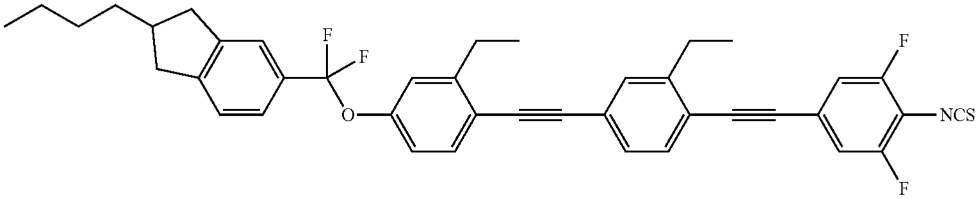
(I-57)
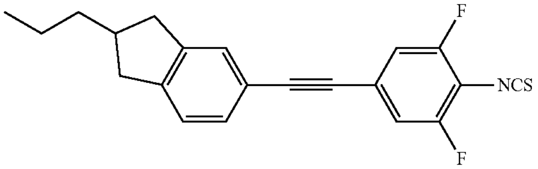
(I-58)
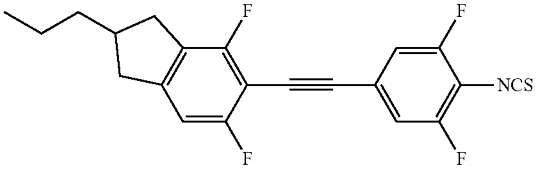
[Chem. 22]
(I-59)
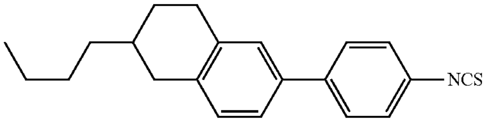
(I-60)
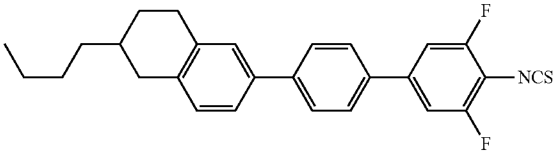

-continued
(I-61)
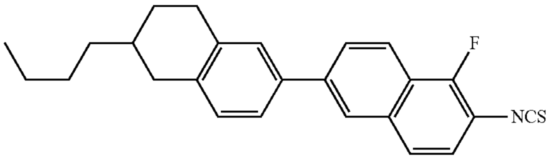
(I-62)
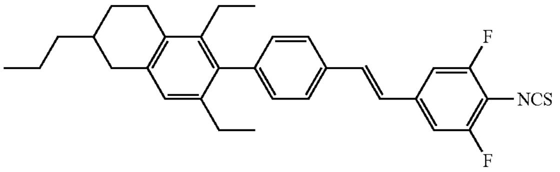
(I-63)
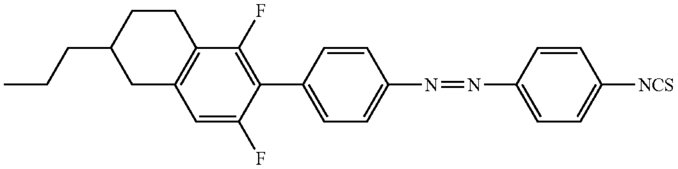
[Chem. 23]
(I-64)
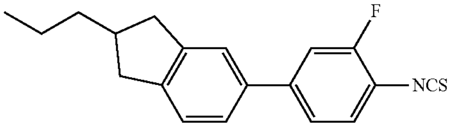
(I-65)
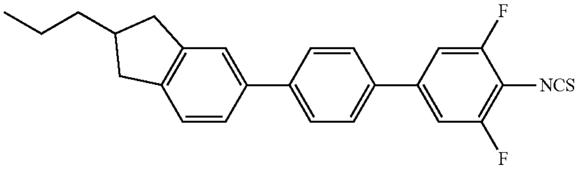
(I-66)
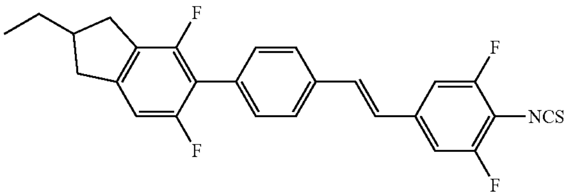
(I-67)
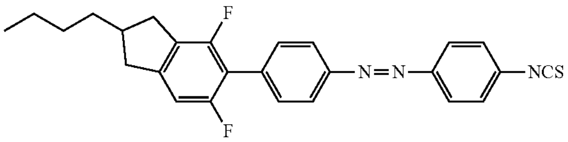
Particularly preferred specific compounds of the compound (including more specific concepts) represented by the general formula (I) include compounds represented by formula (I-68) to formula (I-93) below.
[Chem. 24]
(I-68)
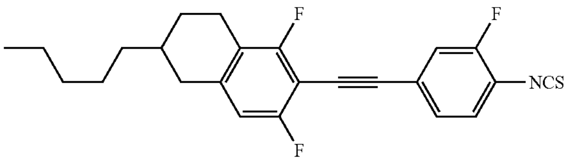
(I-69)
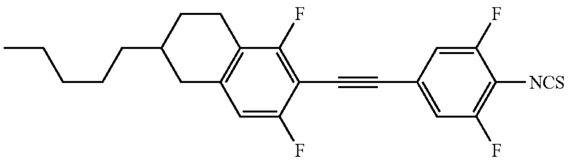
(I-70)
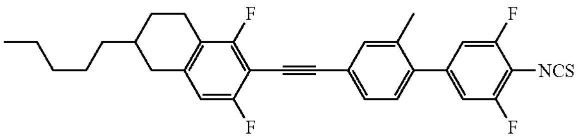
(I-71)
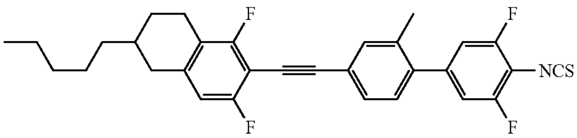
(I-72)
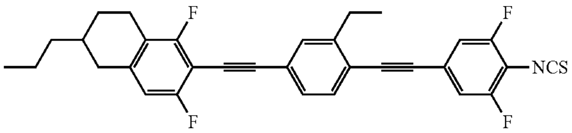
(I-73)
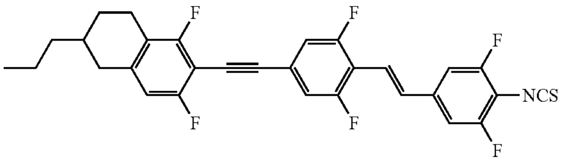

-continued
(I-74)
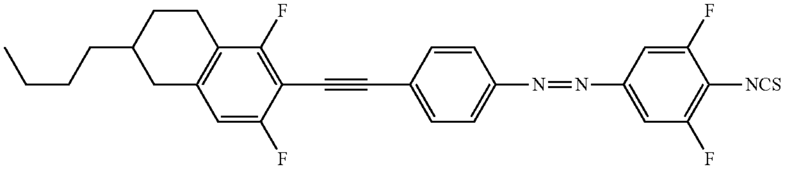
(I-75)
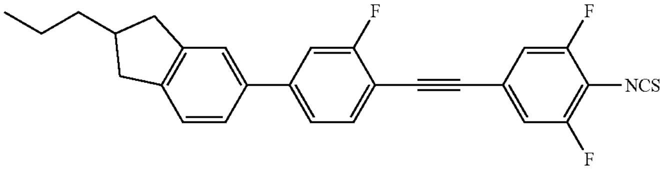
[Chem. 25]
(I-76)
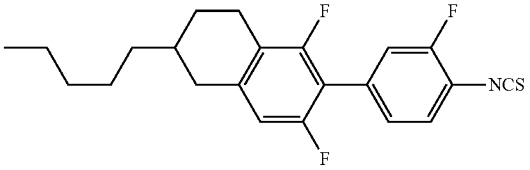
(I-77)
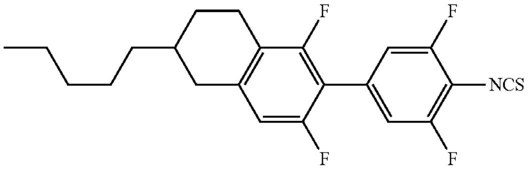
(I-78)
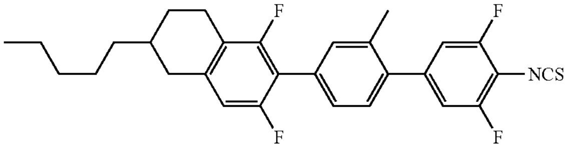
(I-78)
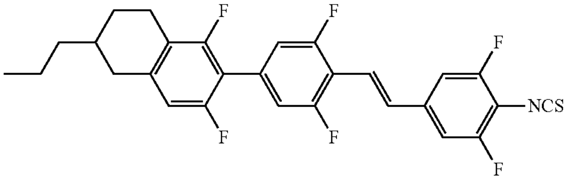
(I-79)
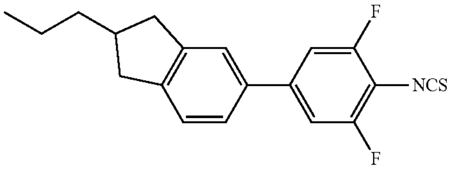
(I-80)
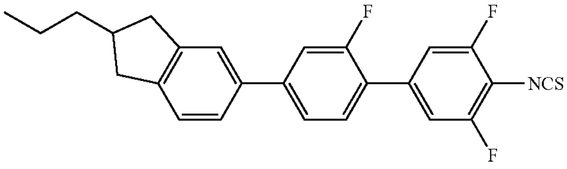
(I-81)
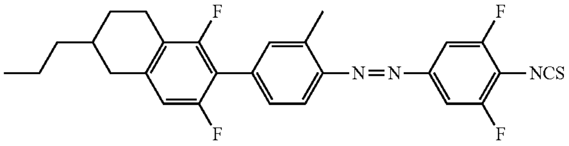
(I-82)
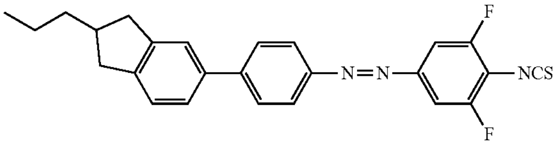
[Chem. 26]
(I-83)
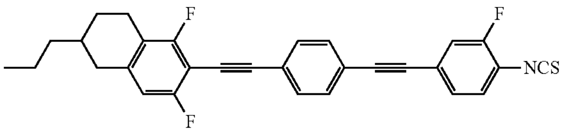
(I-84)
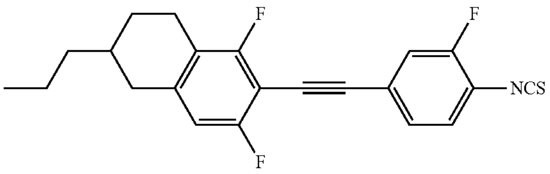
(I-85)
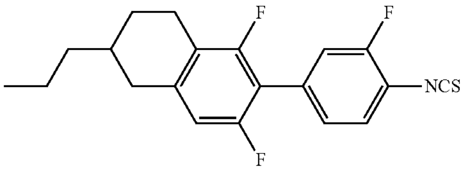
(I-86)
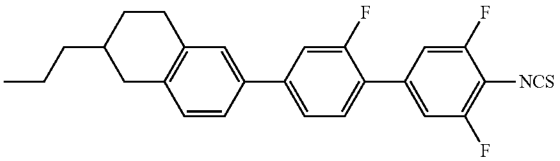

-continued (I-87)

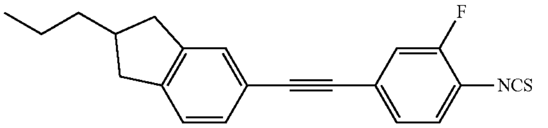

(I-88)

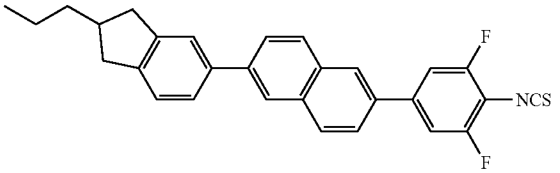

(I-89)

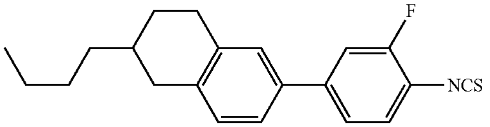

(I-90)

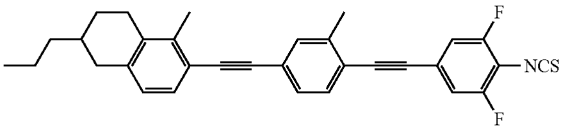

(I-91)

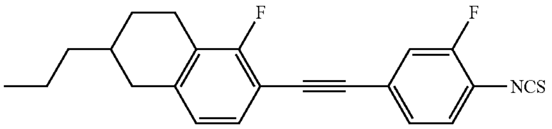

[Chem. 27]

(I-92)

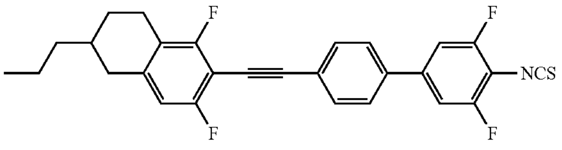

(I-93)

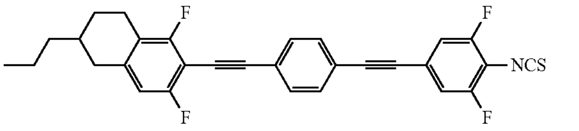

From the viewpoint of a liquid crystal composition having high refractive index anisotropy, the refractive index anisotropy (Δn) of the compound (including more specific concepts) represented by the general formula (I) is preferably 0.15 or more, preferably 0.15 or more and 1.00 or less, preferably 0.20 or more and 0.95 or less, preferably 0.25 or more and 0.90 or less, preferably 0.30 or more and 0.85 or less, and preferably 0.34 or more and 0.80 or less.

From the viewpoint of voltage driving, the dielectric anisotropy (Δε (1 kHz)) at 1 kHz of the compound (including more specific concepts) represented by the general formula (I) is preferably 2 or more, preferably 2 or more and 60 or less, preferably 2.5 or more and 50 or less, preferably 3 or more and 40 or less, and 15 or more and 30 or less.

The compound of the present invention can be produced by a production method below, but another production method can also be used. For example, the method described below for producing an intermediate tetrahydronaphthalene compound (A-1) of the compound of the present invention is disclosed in Japanese Unexamined Patent Application Publication No. 2002-128717, and an indane compound (A-2) can be produced by a production method described below.

[Chem. 28]

(A-1)

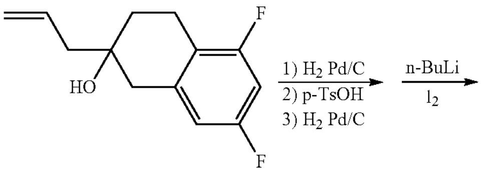

-continued

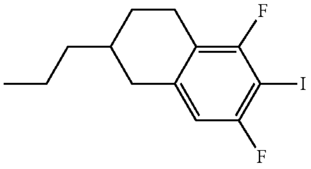

[Chem. 29]

(A-2)

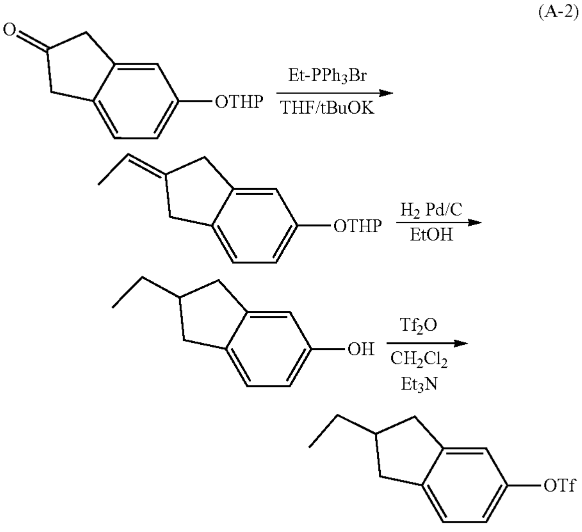

In the present invention, the compound of the general formula (I) can be produced, for example, as described below, but the gist and application range of the present invention are not limited to these.

The compound of the present invention can be produced by a production method below.

(Production Method 1) Production of Compound Represented by Formula (s-6) Below

[Chem. 30]

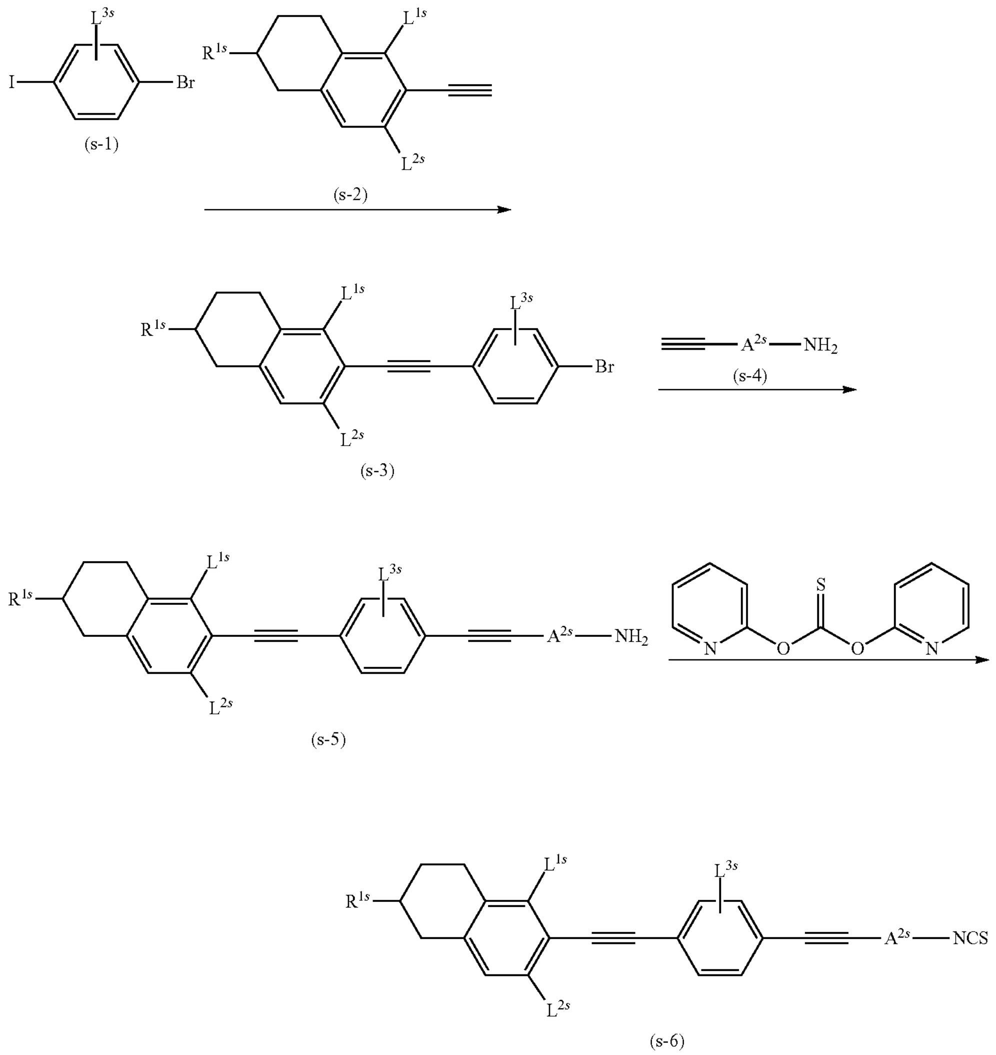

(s-1)

(s-2)

(s-3)

(s-4)

(s-5)

(s-6)

(In the formulae, $R^{1s}$, $A^{2s}$, $L^{1s}$, $L^{2s}$, and $L^{3s}$ represent the same meanings as $R^1$, $A^2$, $L^1$, $L^2$, and $L^3$ in the general formula (I).)

A compound represented by general formula (s-3) can be produced by reacting a compound represented by general formula (s-1) with a compound represented by general formula (s-2). The reaction method is, for example, a Sonogashira coupling reaction using a palladium catalyst, a copper catalyst, and a base. Examples of the palladium catalyst include [1,1'-bis(diphenylphosphino)ferrocene]palladium (II) dichloride, palladium (II) acetate, dichlorobis[di-tert-butyl(p-dimethylaminophenyl)phosphino]palladium (II), dichlorobis(triphenylphosphine)palladium (II), tetrakis (triphenylphosphine)palladium (0), and the like. When palladium (II) acetate is used as the palladium catalyst, a ligand such as triphenylphosphine, 2-dicyclohexylphosphino-2',4',6'-triisopropylbiphenyl, or the like may be added. Examples of the copper catalyst include copper (I) iodide. Examples of the base include triethylamine and the like.

A compound represented by general formula (s-5) can be produced by reacting the compound represented by the general formula (s-3) with a compound represented by general formula (s-4). The reaction method is, for example, a Sonogashira coupling reaction using a palladium catalyst, a copper catalyst, and a base. Examples of the palladium catalyst, the copper catalyst, and the base include those described above. Finally, an objective material (s-6) can be produced by reacting an amino group with a thiocarbamate compound.

(Production Method 2) Production of Compound Represented by Formula (s-12) Below

[Chem. 31]

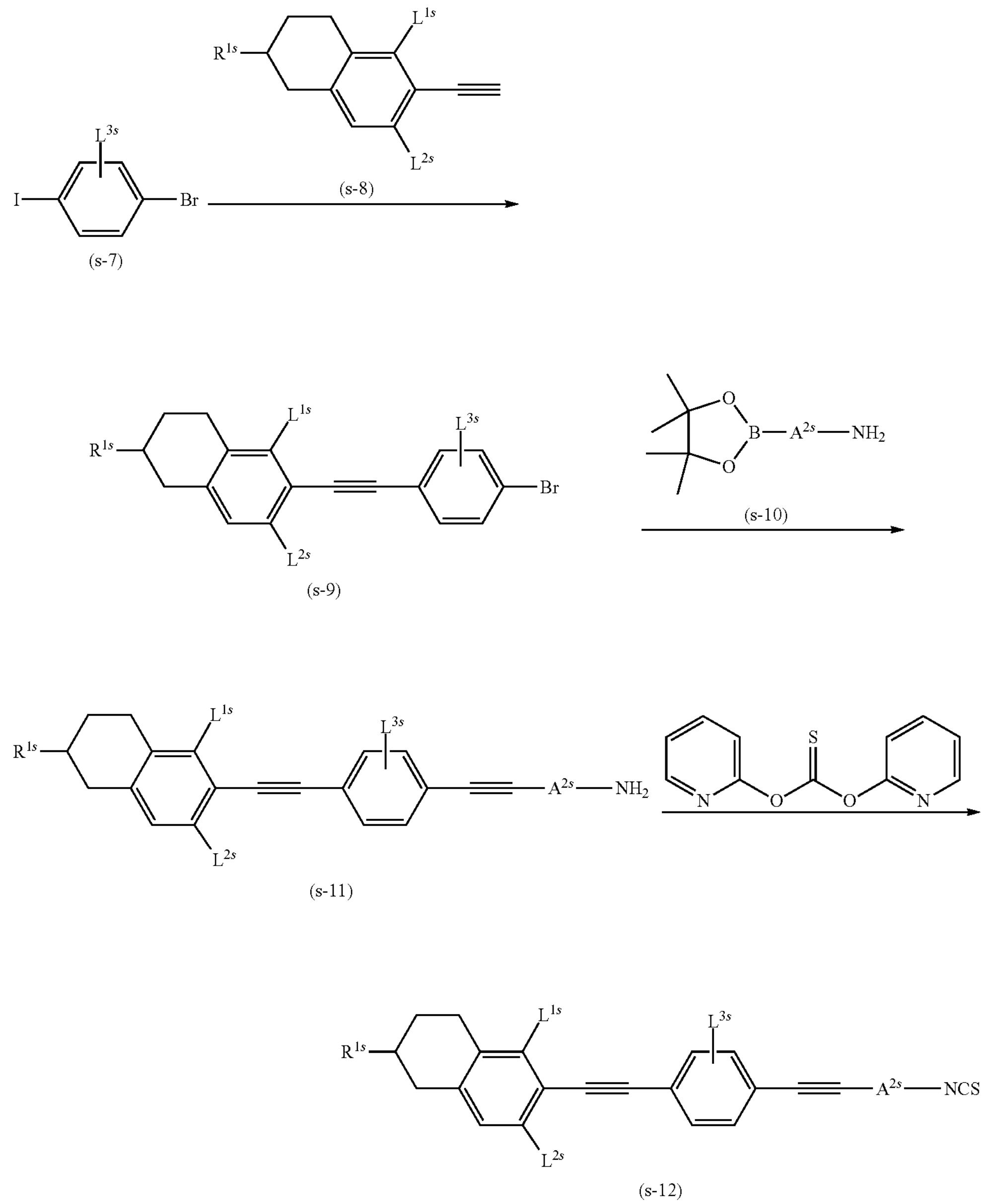

(s-7) (s-8) (s-9) (s-10) (s-11) (s-12)

(In the formulae, $R^{1s}$, $A^{2s}$, $L^{1s}$, $L^{2s}$, and $L^{3s}$ represent the same meanings as $R^1$, $A^2$, $L^1$, $L^2$, and $L^3$ in the general formula I).)

The compound represented by general formula (s-9) can be produced by reacting a compound represented by general formula (s-7) with a compound represented by general formula (s-8). A reaction method is, for example, a Sonogashira coupling reaction using a palladium catalyst, a copper catalyst, and a base. Examples of the palladium catalyst, the copper catalyst, and the base include the compounds described in the production method 1.

A compound represented by general formula (s-11) can be produced by reacting a compound represented by general formula (s-10) with the compound represented by general formula (s-9). The reaction method is, for example, a Suzuki coupling reaction using a palladium catalyst and a base. Examples of the palladium catalyst and the base include compounds described in the production method 1. Other examples of the base include potassium carbonate, sodium carbonate, potassium phosphate, and the like. Finally, an objective material (s-12) can be produced by reacting an amino group with a thiocarbamate compound.

(Production Method 3) Production of Compound Represented by Formula (s-18) Below
[Chem. 32]
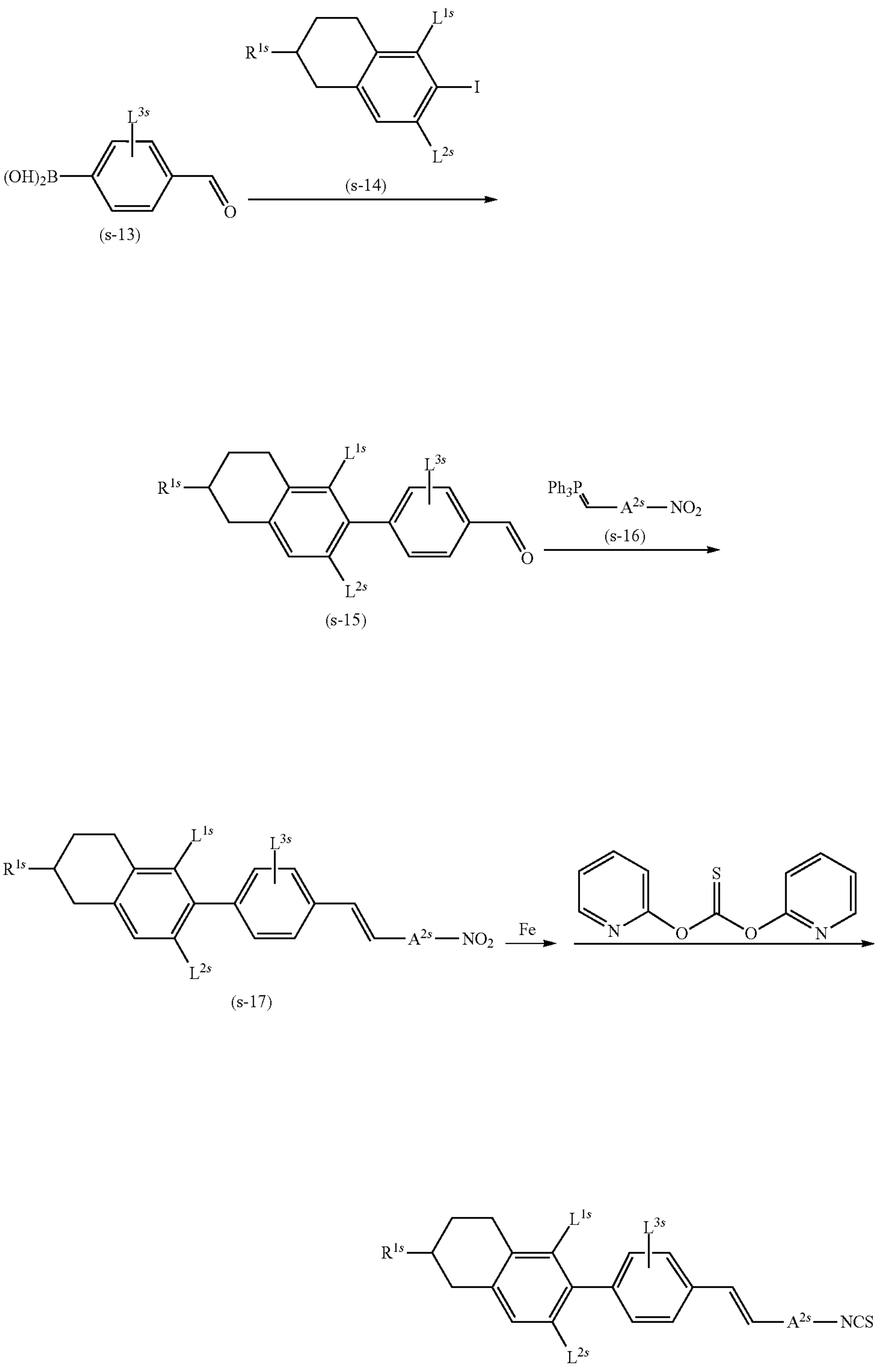
(s-13)
(s-15)
(s-17)
(s-18)

(In the formulae, $R^{1s}$, $A^{2s}$, $L^{1s}$, $L^{2s}$, and $L^{3s}$ represent the same meanings as $R^1$, $A^2$, $L^1$, $L^2$, and $L^3$ in the general formula (I).)

A compound represented by general formula (s-15) can be produced by reacting a compound represented by general formula (s-13) with a compound represented by general formula (s-14). The reaction method is, for example, a Suzuki coupling reaction using a palladium catalyst and a base. Examples of the palladium catalyst and the base include the compounds described in the production method 1.

A compound represented by general formula (s-17) can be produced by reacting the compound represented by the general formula (s-15) with a compound represented by general formula (s-16). The reaction method is, for example, Wittig reaction. Further, an objective material (s-18) can be produced by converting a nitro group to an amino group using iron or the like and then reacting with a thiocarbamate compound.

(Production Method 4) Production of Compound Represented by Formula (s-22) Below

[Chem. 33]

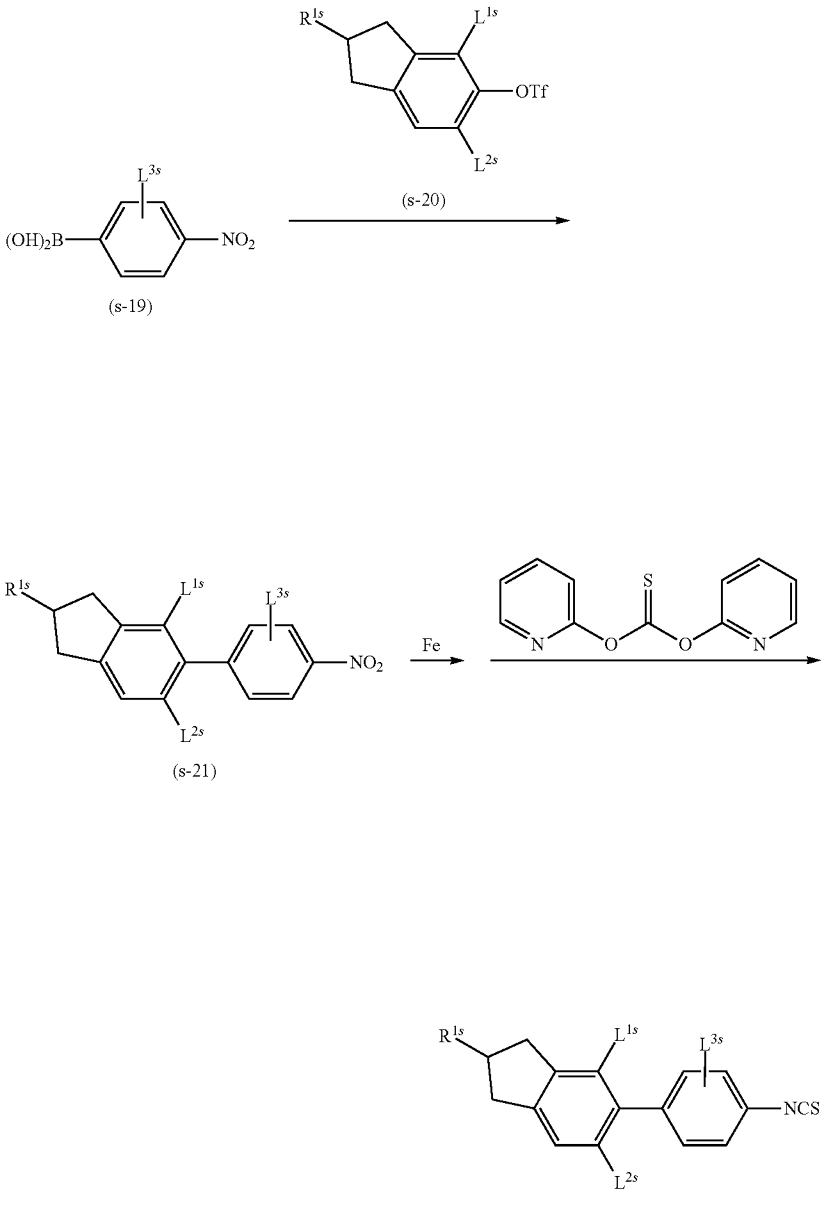

(s-19) (s-20) (s-21) (s-22)

(In the formulae, $R^{1s}$, $L^{1s}$, $L^{2s}$, and $L^{3s}$ represent the same meanings as $R^1$, $L^1$, $L^2$, and $L^3$ in the general formula M.)

A compound represented by general formula (s-21) can be produced by reacting a compound represented by general formula (s-19) with a compound represented by general formula (s-20). The reaction method is, for example, a Suzuki coupling reaction using a palladium catalyst and a base. Examples of the palladium catalyst and the base include the compounds described in the production method 1.

An objective material (s-22) can be produced by converting a nitro group in the general formula (s-21) to an amino group using iron or the like and then reacting with a thiocarbamate compound.

(Production Method 5) Production of Compound Represented by Formula (s-29) Below

[Chem. 34]

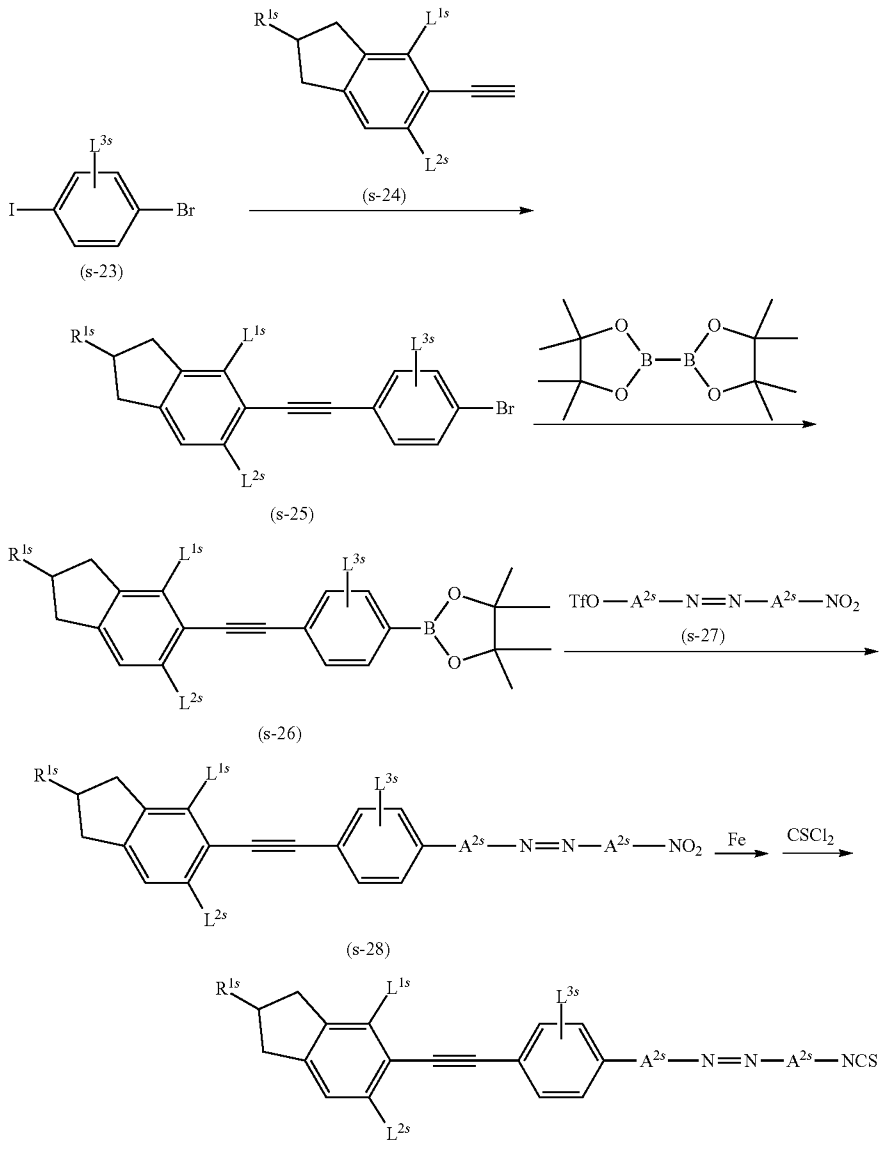

(s-23)

(s-25)

(s-26)

(s-28)

(s-29)

(In the formulae, $R^{1s}$, $A^{2s}$, $L^{1s}$, $L^{2s}$, and $L^{3s}$ represent the same meanings as $R^1$, $A^2$, $L^1$, $L^2$, and $L^3$ in the general formula M.)

A compound represented by general formula (s-25) can be produced by reacting a compound represented by general formula (s-23) with a compound represented by general formula (s-24). The reaction method is, for example, a Sonogashira coupling reaction using a palladium catalyst, a copper catalyst, and a base. Examples of the palladium catalyst, the copper catalyst, and the base include the compounds described in the production method 1.

A compound represented by general formula (s-26) can be produced by reacting the compound represented by the general formula (s-25) with bis(pinacolato) diborane. The reaction method is, for example, a Suzuki coupling reaction using a palladium catalyst and a base. Examples of the palladium catalyst and the base include the compounds described in the production method 1.

A compound represented by general formula (s-28) can be produced by reacting the compound represented by the general formula (s-26) with a compound represented by general formula (s-27). The reaction method is, for example, a Suzuki coupling reaction using a palladium catalyst and a base. Examples of the palladium catalyst and the base include the compounds described in the production method 1.

Further, an objective material (s-29) can be produced by converting a nitro group of the compound represented by the general formula (s-28) to an amino group using iron or the like and then reacting with thiophosgene.

Examples of the reaction conditions other than those described in each of the steps include those described in documents such as Experimental Chemical Course (edited by Chemical Society of Japan, issued by Maruzen Co., Ltd.), Organic Syntheses (A John Wiley & Sons, Inc., Publication), Beilstein Handbook of Organic Chemistry (Beilstein-Institut fuer Literatur der Organischen Chemie, Springer-Verlag Berlin and Heidelberg GmbH & Co. K), Fiesers' Reagents for Organic Synthesis (John Wiley & Sons, Inc.), and the like, and those published in databases such as SciFinder (Chemical Abstracts Service, American Chemical Society), Reaxys (Elsevier Ltd.), and the like.

If required, a functional group can be protected in each of the steps. Examples of a protective group include protective groups described in GREENE'S PROTECTIVE GROUPS IN ORGANIC SYNTHESIS ((Fourth Edition), co-authored by PETER G. M. WUTS and THEODORA W. GREENE, A John Wiley & Sons, Inc., Publication) and the like.

If required, purification can be performed in each of the steps. Examples of a purification method include chromatography, recrystallization, distillation, sublimation, reprecipitation, adsorption, liquid separation treatment, and the like. Examples of a purifying agent include silica gel, alumina, activated carbon, and the like.

Next, a composition containing the compound (including more specific concepts) represented by the general formula (I) is described.

The composition is preferably a liquid crystal composition.

That is, the compound (including more specific concepts) represented by the general formula (I) is preferably used by adding to a liquid crystal composition. When a liquid crystal composition contains the compound (including more specific concepts) represented by the general formula (I), the liquid crystal composition may contain one compound including more specific concepts represented by the general formula (I) or contain a plurality of compounds including more specific concepts represented by the general formula (I). That is, the liquid crystal composition contains one or two or more compounds (including more specific concepts) represented by the general formula (I). When the liquid crystal composition of the present invention contains the compound (including more specific concepts) represented by the general formula (I), the total content of the compound (including more specific concepts) represented by the general formula (I) in 100% by mass of the liquid crystal composition is preferably 5% by mass or more, more preferably 10% by mass or more and 95% by mass or less, still more preferably 15% by mass or more and 90% by mass or less, and particularly preferably 20% by mass or more and 85% by mass or less. When the liquid crystal composition contains a compound (including more specific concepts) represented by the general formula (I), the "total content of the compound (including more specific concepts) represented by the general formula (I)" represents the content of the compound (including more specific concepts) represented by the general formula (I), while when the liquid crystal composition contains a plurality of compounds (including more specific concepts) represented by the general formula (I), the total content represents the total content of the plurality of compounds represented by the general formula (I) including more specific concepts.

The refractive index anisotropy ($\Delta n$) of the liquid crystal composition containing the compound (including more specific concepts) represented by the general formula (I) is preferably 0.15 or more and preferably 0.15 or more and 1.00 or less. From the viewpoint of the liquid crystal phase temperature range, driving voltage, rotational viscosity, and elastic modulus of the liquid crystal composition, the refractive index anisotropy ($\Delta n$) is preferably 0.20 or more and 0.95 or less, more preferably 0.25 or more and 0.90 or less, still more preferably 0.30 or more and 0.85 or less, and particularly preferably 0.34 or more and 0.80 or less.

The compound (including more specific concepts) represented by the general formula (I) may be used by adding to a liquid crystal composition having positive, neutral, or negative dielectric anisotropy ($\Delta\varepsilon$), and the dielectric anisotropy can be adjusted to intended dielectric anisotropy ($\Delta\varepsilon$).

The dielectric anisotropy ($\Delta\varepsilon$ (1 kHz)) at 1 kHz of the liquid crystal composition containing the compound (including more specific concepts) represented by the general formula (I) is preferably 2 or more and preferably 2 or more and 60 or less. From the viewpoint of the liquid crystal phase temperature range, storage stability, weather resistance, driving voltage, rotational viscosity, and elastic modulus of the liquid crystal composition, the dielectric anisotropy ($\Delta\varepsilon$ (1 kHz)) at 1 kHz is preferably 2.5 or more and 50 or less, more preferably 3 or more and 40 or less, and particularly preferably 15 or more and 30 or less.

The liquid crystal composition containing the compound (including more specific concepts) represented by the general formula (I) may be used by adding to a liquid crystal composition having neutral or negative dielectric anisotropy ($\Delta\varepsilon$). In this case, the dielectric anisotropy ($\Delta\varepsilon$ (1 kHz)) at 1 kHz of the liquid crystal composition containing the compound (including more specific concepts) represented by the general formula (I) is preferably 2 or less and preferably −20 or more and less than 2. From the viewpoint of the liquid crystal phase temperature range, storage stability, weather resistance, driving voltage, rotational viscosity, and elastic modulus of the liquid crystal composition, the dielectric anisotropy ($\Delta\varepsilon$ (1 kHz)) at 1 kHz is preferably −15 or more and 1.5 or less, more preferably −10 or more and 1 or less, and particularly preferably −5 or more and 0.5 or less.

The liquid crystal composition containing the compound (including more specific concepts) represented by the general formula (I) can be used for an element of a device such as a high-frequency phase shifter, a phased array antenna, an image recognition device, a distance measuring device, a liquid crystal display device, a liquid crystal lens, a birefringent lens for stereoscopic image display, or the like.

The frequency range of an element used in a high-frequency phase shifter or a phased array antenna is preferably 1 MHz or more and 1 THz or less, more preferably 1 GHz or more and 500 GHz or less, still more preferably 2 GHz or more and 300 GHz or less, and particularly preferably 5 GHz or more and 150 GHz or less.

When the liquid crystal composition containing the compound (including more specific concepts) represented by the general formula (I) has positive dielectric anisotropy ($\Delta\varepsilon$), the liquid crystal composition preferably contains a compound represented by general formula (VI) below.

[Chem. 35]

(VI)

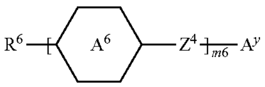

(In the formula, $R^6$ represents an alkyl group having 1 to 8 carbon atoms, an alkoxy group having 1 to 7 carbon atoms, an alkenyl group having 2 to 8 carbon atoms, or an alkenyloxy group having 2 to 7 carbon atoms, $A^6$ represents a group selected from formula (A6-1) to formula (A6-8) below

[Chem. 36]

(A6-1)

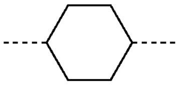

(A6-2)

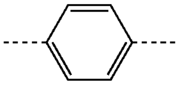

(A6-3)

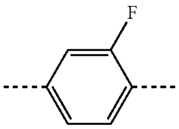

(A6-4)

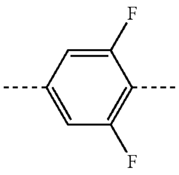

(A6-5)

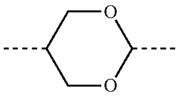

(A6-6)

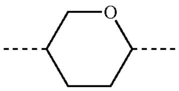

-continued (A6-7)

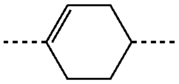

(A6-8)

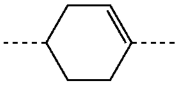

(in the formulae, a broken line represents a bond position), when a plurality of $A^6$ are present, they may be the same or different, $Z^4$ represents $-O-$, $-S-$, $-OCH_2-$, $-CH_2O-$, $-CH_2CH_2-$, $-CO-$, $-COO-$, $-COO-$, $-CO-S-$, $-S-CO-$, $-O-CO-O-$, $-CO-NH-$, $-NH-CO-$, $-OCO-NH-$, $-NH-COO-$, $-NH-CO-NH-$, $-NH-O-$, $-O-NH-$, $-SCH_2-$, $-CH_2S-$, $-CF_2O-$, $-OCF_2-$, $-CF_2S-$, $-SCF_2-$, $-CH{=}CH-COO-$, $-CH{=}CH-OCO-$, $-COO-CH{=}CH-$, $-OCO-CH{=}CH-$, $-COO-CH_2CH_2-$, $-COO-CH_2CH_2-$, $-CH_2CH_2-COO-$, $-CH_2CH_2-OCO-$, $-COO-CH_2-$, $-COO-CH_2-$, $-CH_2-COO-$, $-CH_2-OCO-$, $-CH{=}CH-$, $-N{=}N-$, $-CH{=}N-$, $-N{=}CH-$, $-CH{=}N-N{=}CH-$, $-CF{=}CF-$, $-C\equiv C-$, or a single bond, and when a plurality of $Z^4$ are present, they may be the same or different, m6 represents an integer of 1 to 4, and $A^y$ represents a group selected from formula (Ay-1) and formula (Ay-2) below

[Chem. 37]

(Ay-1)

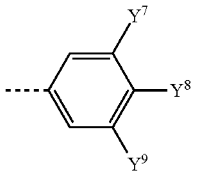

(Ay-2)

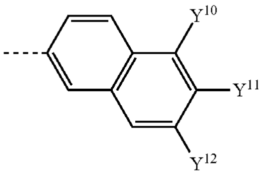

(in the formulae, a broken line represents a bond position, $Y^7$, $Y^9$, $Y^{10}$, and $Y^{12}$ each independently represent a hydrogen atom, a fluorine atom, or a chlorine atom, $Y^8$ and $Y^{11}$ each independently represent a fluorine atom, a chlorine atom, a cyano group, a thioisocyano group, a nitro group, a pentafluorosulfanyl group, an alkyl group having 1 to 8 carbon atoms in which any hydrogen atom may be substituted by a fluorine atom, an alkoxy group having 1 to 7 carbon atoms in which any hydrogen atom may be substituted by a fluorine atom, an alkenyl group having 2 to 8 carbon atoms in which any hydrogen atom may be substituted by a fluorine atom, or an alkenyloxy group having 2 to 7 carbon atoms in which any hydrogen atom may be substituted by a fluorine atom, and in these groups, one $-CH_2-$ or two or more $-CH_2-$ may be each independently substituted by —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—).

From the viewpoint of the liquid crystal phase temperature range, refractive index anisotropy, dielectric anisotropy, rotational viscosity, and elastic modulus of the liquid crystal composition, the compound represented by the general formula (VI) is preferably a compound represented by general formula (VI-i) below.

[Chem. 38]

(VI-i)

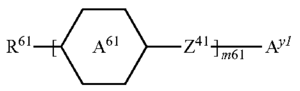

(In the formula, $R^{61}$ represents an alkyl group having 1 to 5 carbon atoms, an alkoxy group having 1 to 4 carbon atoms, an alkenyl group having 2 to 5 carbon atoms, or an alkenyloxy group having 2 to 4 carbon atoms, $A^{61}$ represents a group selected from the formula (A6-1) to the formula (A6-6), and when a plurality of $A^{61}$ are present, they may be the same or different, $Z^{41}$ represents $-OCH_2-$, $-CH_2O-$, $-CH_2CH_2-$, —COO—, —OCO—, $-CF_2O-$, $-OCF_2-$, —CH═CH—COO—, —OCO—CH═CH—, —CH═CH—, —CH═N—N═CH—, —CF═CF—, —N═N—, —C≡C—, or a single bond, and when a plurality of $Z^{41}$ are present, they may be the same or different, m61 represents an integer of 1 to 3, and $A^{y1}$ represents a group selected from formula (Ay-1-i) and formula (Ay-2-i) below

[Chem. 39]

(Ay-1-i)

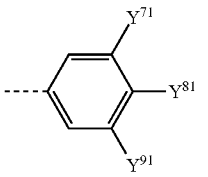

(Ay-2-i)

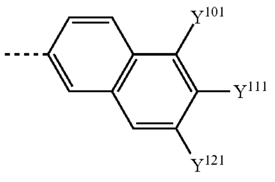

(in the formulae, a broken line represents a bond position, $Y^{71}$, $Y^{91}$, $Y^{101}$, and $Y^{121}$ each independently represent a hydrogen atom, a fluorine atom, or a chlorine atom, $Y^{81}$ and $Y^{111}$ each independently represent a fluorine atom, a chlorine atom, a cyano group, a thioisocyano group, a nitro group, a pentafluorosulfanyl group, an alkyl group having 1 to 8 carbon atoms in which any hydrogen atom may be substituted by a fluorine atom, an alkoxy group having 1 to 7 carbon atoms in which any hydrogen atom may be substituted by a fluorine atom, an alkenyl group having 2 to 8 carbon atoms in which any hydrogen atom may be substituted by a fluorine atom, or an alkenyloxy group having 2 to 7 carbon atoms in which any hydrogen atom may be substituted by a fluorine atom). The compound represented by the general formula (VI) is more preferably a compound represented by general formula (VI-ii) below.

[Chem. 40]

(VI-ii)

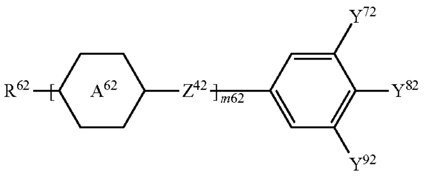

(In the formula, $R^{62}$ represents an alkyl group having 1 to 5 carbon atoms, an alkoxy group having 1 to 4 carbon atoms, an alkenyl group having 2 to 5 carbon atoms, or an alkenyloxy group having 2 to 4 carbon atoms, $A^{62}$ represents a group selected from the formula (A6-1) to the formula (A6-5), and when a plurality of $A^{62}$ are present, they may be the same or different, $Z^{42}$ represents $-CF_2O-$, $-OCF_2-$, —CH═CH—, —CF═CF—, —N═N—, —C≡C—, or a single bond, and when a plurality of $Z^{42}$ are present, they may be the same or different, m62 represents 1, 2, or 3, $Y^{72}$ and $Y^{92}$ each independently represent a hydrogen atom, a fluorine atom, or a chlorine atom, and $Y^{82}$ represents a fluorine atom, a chlorine atom, a cyano group, a thioisocyano group, a nitro group, a pentafluorosulfanyl group, an alkyl group having 1 to 8 carbon atoms in which any hydrogen atom may be substituted by a fluorine atom, an alkoxy group having 1 to 7 carbon atoms in which any hydrogen atom may be substituted by a fluorine atom, an alkenyl group having 2 to 8 carbon atoms in which any hydrogen atom may be substituted by a fluorine atom, or an alkenyloxy group having 2 to 7 carbon atoms in which any hydrogen atom may be substituted by a fluorine atom). The compound represented by the general formula (VI) is still more preferably a compound represented by general formula (VI-iii) below.

[Chem. 41]

(VI-iii)

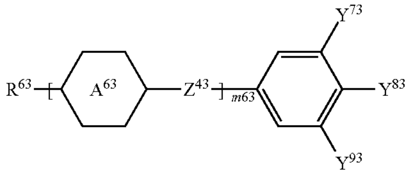

(In the formula, $R^{63}$ represents an alkyl group having 1 to 5 carbon atoms, an alkoxy group having 1 to 4 carbon atoms, or an alkenyl group having 2 to 5 carbon atoms, $A^{63}$ represents a group selected from the formula (A6-1) to the formula (A6-5), and when a plurality of $A^{63}$ are present, they may be the same or different, $Z^{43}$ represents —$CF_2O$—, —$OCF_2$—, —N═N—, —C≡C—, or a single bond, and when a plurality of $Z^{43}$ are present, they may be the same or different, m63 represents 1, 2, or 3, $Y^{73}$ and $Y^{93}$ each independently represent a hydrogen atom, a fluorine atom, or a chlorine atom, and $Y^{83}$ represents a fluorine atom, a chlorine atom, a cyano group, or a thioisocyano group). The compound represented by the general formula (VI) is particularly preferably a compound represented by general formula (VI-iv-1) to general formula (VI-iv-21) below.

[Chem. 42]

(VI-iv-1)

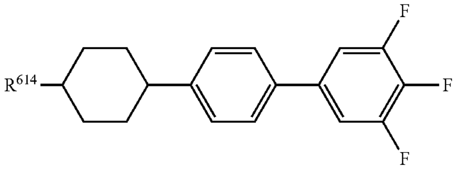

(VI-iv-2)

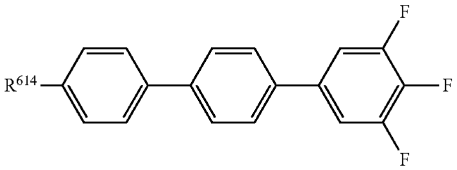

(VI-iv-3)

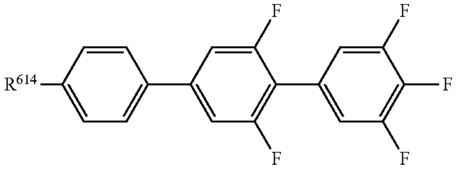

(VI-iv-4)

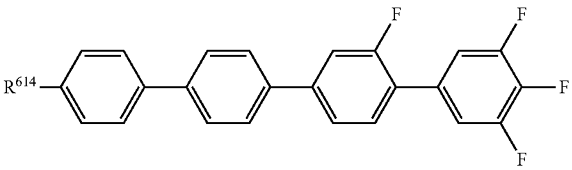

[Chem. 43]

(VI-iv-5)

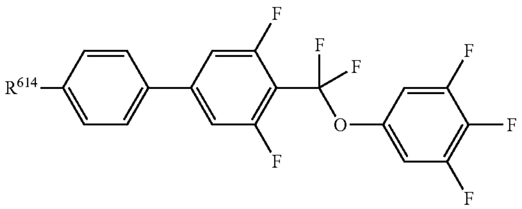

-continued (VI-iv-6)

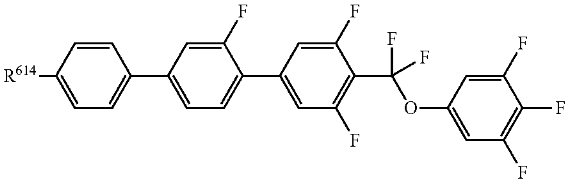

(VI-iv-7)

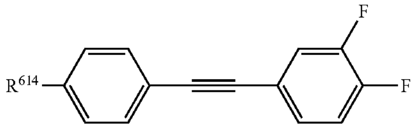

(VI-iv-8)

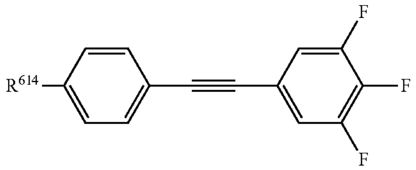

[Chem. 44]

(VI-iv-9)

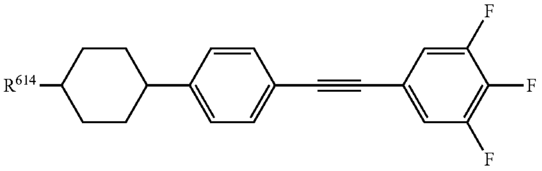

(VI-iv-10)

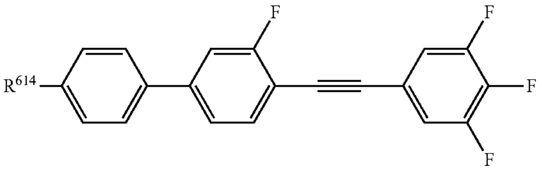

(VI-iv-11)

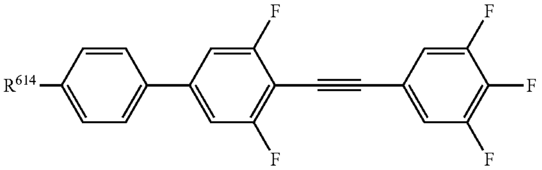

(VI-iv-12)

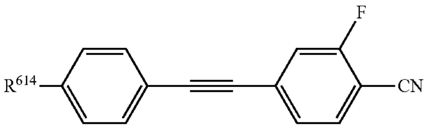

[Chem. 45]

(VI-iv-13)

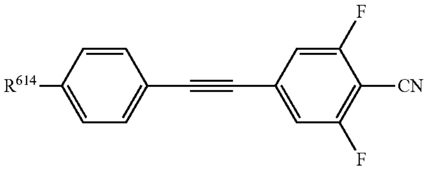

-continued (VI-iv-14)

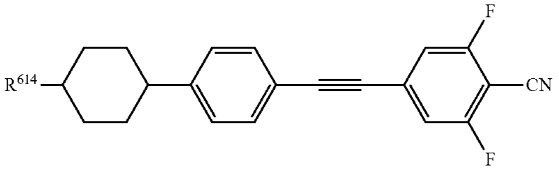

(VI-iv-15)

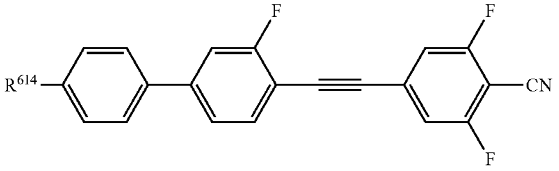

(VI-iv-16)

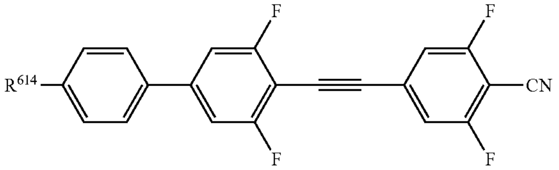

[Chem. 46]

(VI-iv-17)

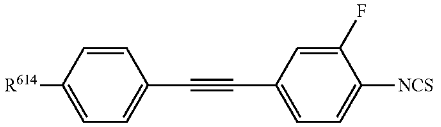

(VI-iv-18)

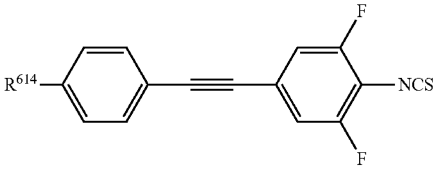

(VI-iv-19)

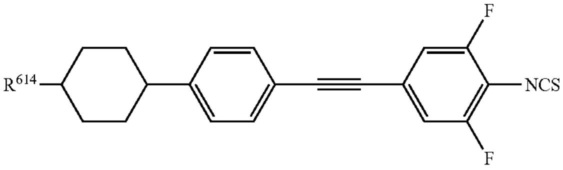

(VI-iv-20)

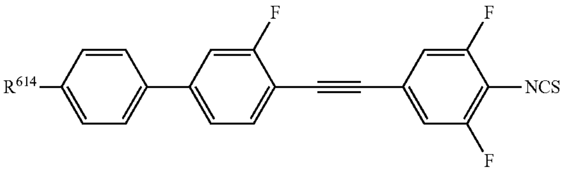

(VI-iv-21)

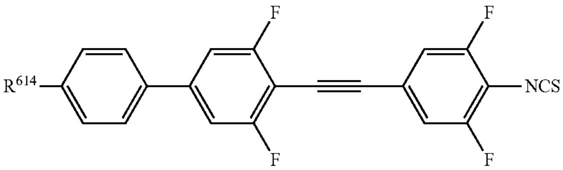

(In the formulae, $R^{614}$ represents an alkyl group having 1 to 5 carbon atoms, an alkoxy group having 1 to 4 carbon atoms, or an alkenyl group having 2 to 5 carbon atoms.)

The liquid crystal composition containing the compound (including more specific concepts) represented by the general formula (I) may contain a compound represented by general formula (III) below.

[Chem. 47]

(III)

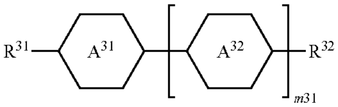

(In the formula, $R^{31}$ and $R^{32}$ each independently represent an alkyl group having 1 to 8 carbon atoms, an alkoxy group having 1 to 7 carbon atoms, an alkenyl group having 2 to 8 carbon atoms, or an alkenyloxy group having 2 to 7 carbon atoms, $A^{31}$ and $A^{32}$ each independently represent a group selected from formula (A3-1) to formula (A3-8) below,

[Chem. 48]

(A3-1)

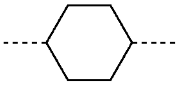

(A3-2)

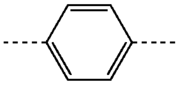

(A3-3)

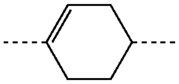

(A3-4)

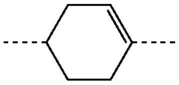

(A3-5)

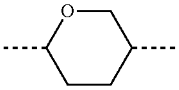

(A3-6)

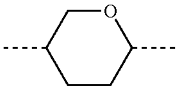

(A3-7)

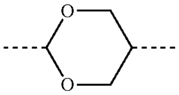

(A3-8)

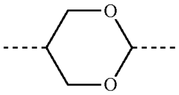

(in the formulae, a broken line represents a bond position), when a plurality of $A^{32}$ are present, they may be the same or different, and m31 represents an integer of 1 to 4).

From the viewpoint of the liquid crystal phase temperature range, refractive index anisotropy, dielectric anisotropy, rotational viscosity, and elastic modulus of the liquid crystal composition, the compound represented by the general formula (III) is preferably a compound represented by general formula (III-i) below.

[Chem. 49]

(III-i)

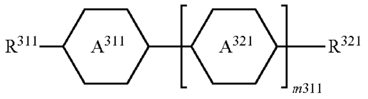

(In the formula, $R^{311}$ and $R^{321}$ each independently represent an alkyl group having 1 to 5 carbon atoms, an alkoxy group having 1 to 4 carbon atoms, an alkenyl group having 2 to 5 carbon atoms, or an alkenyloxy group having 2 to 4 carbon atoms, $A^{311}$ and $A^{321}$ each independently represent a group selected from formula (A31-1) to formula (A31-6) below,

[Chem. 50]

(A31-1)

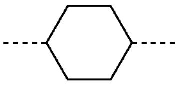

(A31-2)

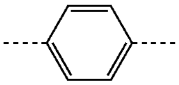

(A31-3)

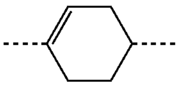

(A31-4)

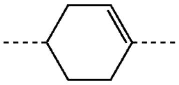

(A31-5)

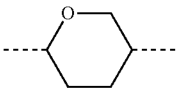

(A31-6)

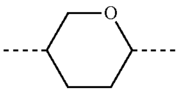

(in the formulae, a broken line represents a bond position), when a plurality of $A^{321}$ are present, they may be the same or different, and m311 represents an integer of 1 to 3).

The compound represented by the general formula (III) is more preferably a compound represented by general formula (III-ii) below.

[Chem. 51]

(III-ii)

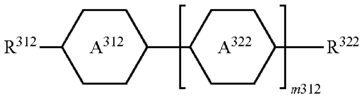

(In the formula, $R^{312}$ and $R^{322}$ each independently represent an alkyl group having 1 to 5 carbon atoms, an alkoxy group having 1 to 4 carbon atoms, an alkenyl group having 2 to 5 carbon atoms, or an alkenyloxy group having 2 to 4 carbon atoms, $A^{312}$ and $A^{322}$ each independently represent a group selected from formula (A32-1) to formula (A32-4) below,

[Chem. 52]

(A32-1)

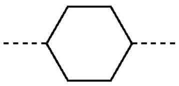

(A32-2)

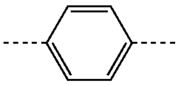

(A32-3)

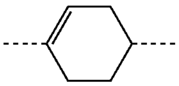

(A32-4)

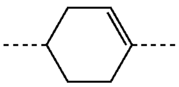

(in the formulae, a broken line represents a bond position), when a plurality of $A^{322}$ are present, they may be the same or different, and m312 represents 1 or 2).

The compound represented by the general formula (III) is still more preferably a compound represented by general formula (III-iii) below.

[Chem. 53]

(III-iii)

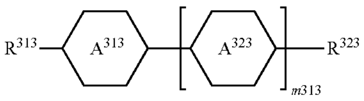

(In the formula, $R^{313}$ and $R^{323}$ each independently represent an alkyl group having 1 to 5 carbon atoms, an alkoxy group having 1 to 4 carbon atoms, or an alkenyl group having 2 to 5 carbon atoms, $A^{313}$ and $A^{323}$ each independently represent a group selected from formula (A33-1) and formula (A33-2) below,

[Chem. 54]

(A33-1)

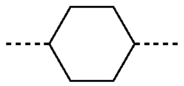

(A33-2)

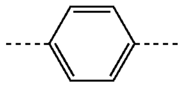

(in the formulae, a broken line represents a bond position), when a plurality of $A^{323}$ are present, they may be the same or different, and m313 represents 1 or 2).

Specifically, the compound represented by the general formula (III) is particularly preferably a compound represented by general formula (III-iv-1) to general formula (III-iv-10) below.

[Chem. 55]

(III-iv-1)

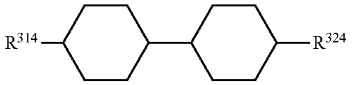

(III-iv-2)

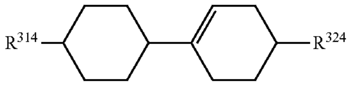

(III-iv-3)

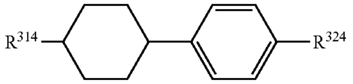

(III-iv-4)

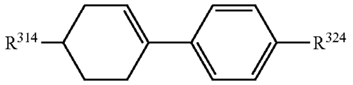

(III-iv-5)

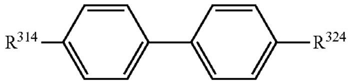

[Chem. 56]

(III-iv-6)

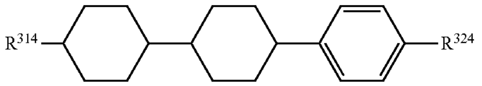

(III-iv-7)

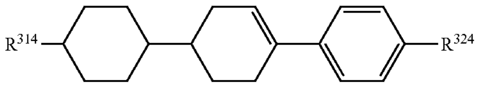

(III-iv-8)

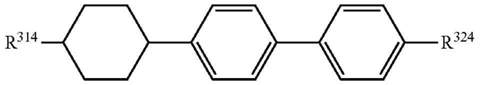

(III-iv-9)

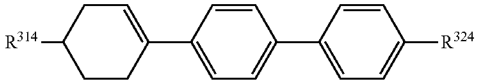

-continued (III-iv-10)

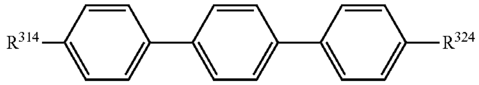

(In the formulae, $R^{314}$ and $R^{324}$ each independently represent an alkyl group having 1 to 5 carbon atoms, an alkoxy group having 1 to 4 carbon atoms, or an alkenyl group having 2 to 5 carbon atoms, When the liquid crystal composition containing the compound (including more specific concepts) represented by the general formula (I) has neutral or negative dielectric anisotropy (Δε), the liquid crystal composition may contain a compound represented by general formula (IV) below.

[Chem. 57]

(IV)

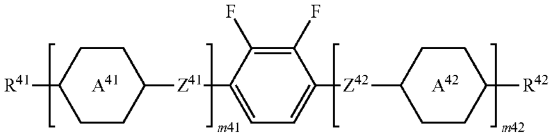

(In the formula, $R^{41}$ and $R^{42}$ each independently represent an alkyl group having 1 to 8 carbon atoms, an alkoxy group having 1 to 7 carbon atoms, an alkenyl group having 2 to 8 carbon atoms, or an alkenyloxy group having 2 to 7 carbon atoms, $A^{41}$ and $A^{42}$ each independently represent a group selected from formula (A4-1) to formula (A4-11) below,

[Chem. 58]

(A4-1)

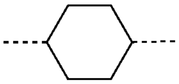

(A4-2)

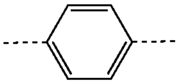

(A4-3)

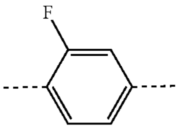

(A4-4)

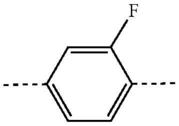

(A4-5)

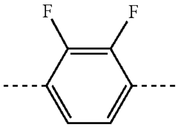

-continued (A4-6)

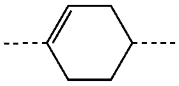

(A4-7)

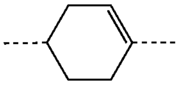

(A4-8)

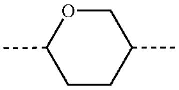

(A4-9)

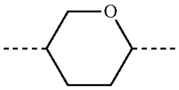

(A4-10)

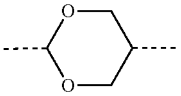

(A4-11)

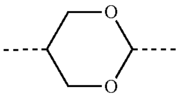

(in the formulae, a broken line represents a bond position), when a plurality of $A^{41}$ are present, they may be the same or different, when a plurality of $A^{42}$ are present, they may be the same or different, $Z^{41}$ and $Z^{42}$ each independently represent —O—, —S—, $—OCH_2—$, $—CH_2O—$, $—CH_2CH_2—$, —CO—, —COO—, —OCO—, —CO—S—, —S—CO—, —O—CO—O—, —CO—NH—, —NH—CO—, OCO—NH—, —NH—COO—, —NH—CO—NH—, —NH—O—, —O—NH—, $—SCH_2—$, $—CH_2S—$, $—CF_2O—$, $—OCF_2—$, $—CF_2S—$, $—SCF_2—$, —CH═CH—COO—, —CH═CH—OCO—, —COO—CH═CH—, —OCO—CH═CH—, $—COO—CH_2CH_2—$, $—COO—CH_2CH_2—$, $—CH_2CH_2—COO—$, $—CH_2CH_2—OCO—$, $—COO—CH_2—$, $—COO—CH_2—$, $—CH_2—COO—$, $—CH_2—OCO—$, —CH═CH—, —N═N—, —CH═N—, —N═CH—, —CH═N—N═CH—, —CF═CF—, —C≡C—, or a single bond, when a plurality of $Z^{41}$ are present, they may be the same or different, when a plurality of $Z^{42}$ are present, they may be the same or different, m41 and m42 each independently represent an integer of 0 to 3, and m41+m42 represents an integer of 1 to 3).

From the viewpoint of the liquid crystal phase temperature range, refractive index anisotropy, dielectric anisotropy, rotational viscosity, and elastic modulus of the liquid crystal composition, the compound represented by the general formula (IV) is preferably a compound represented by general formula (IV-i) below.

[Chem. 59]

(IV-i)

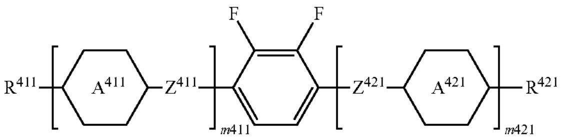

(In the formula, $R^{411}$ and $R^{421}$ each independently represent an alkyl group having 1 to 5 carbon atoms, an alkoxy group having 1 to 4 carbon atoms, an alkenyl group having 2 to 5 carbon atoms, or an alkenyloxy group having 2 to 4 carbon atoms, $A^{411}$ and $A^{421}$ each independently represent a group selected from the formula (A4-1) to the formula (A4-9), when a plurality of $A^{411}$ are present, they may be the same or different, when a plurality of $A^{421}$ are present, they may be the same or different, $Z^{411}$ and $Z^{421}$ each independently represent $—OCH_2—$, $—CH_2O—$, $—CH_2CH_2—$, —COO—, —OCO—, $—CF_2O—$, $—OCF_2—$, —CH═CH—COO—, —OCO—CH═CH—, —CH═CH—, —CH═N—N═CH—, —CF═CF—, —C≡C—, or a single bond, when a plurality of $Z^{411}$ are present, they may be the same or different, when a plurality of $Z^{421}$ are present, they may be the same or different, m411 and m421 each independently represent an integer of 0 to 3, and m411+m421 represents an integer of 1 to 3).

The compound represented by the general formula (IV) is more preferably a compound represented by general formula (IV-ii) below.

[Chem. 60]

(IV-ii)

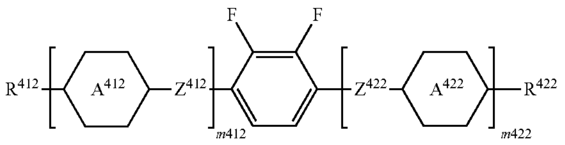

(In the formula, $R^{412}$ and $R^{422}$ each independently represent an alkyl group having 1 to 5 carbon atoms, an alkoxy group having 1 to 4 carbon atoms, an alkenyl group having 2 to 5 carbon atoms, or an alkenyloxy group having 2 to 4 carbon atoms, $A^{412}$ and $A^{422}$ each independently represent a group selected from the formula (A4-1) to the formula (A4-7), when a plurality of $A^{412}$ are present, they may be the same or different, when a plurality of $A^{422}$ are present, they may be the same or different, $Z^{412}$ and $Z^{422}$ each independently represent $—OCH_2—$, $—CH_2O—$, $—CH_2CH_2—$, —COO—, —OCO—, $—CF_2O—$, $—OCF_2—$, or a single bond, when a plurality of $Z^{412}$ are present, they may be the same or different, when a plurality of $Z^{422}$ are present, they may be the same or different, m412 and m422 each independently represent 0, 1, or 2, and m412+m422 represents 1 or 2).

The compound represented by the general formula (IV) is still more preferably a compound represented by general formula (IV-iii) below.

[Chem. 61]

(IV-iii)

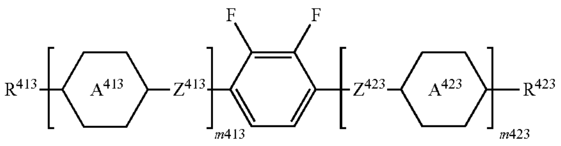

(In the formula, $R^{413}$ and $R^{423}$ each independently represent an alkyl group having 1 to 5 carbon atoms, an alkoxy group having 1 to 4 carbon atoms, or an alkenyl group having 2 to 5 carbon atoms, $A^{413}$ and $A^{423}$ each independently represent a group selected from the formula (A4-1) to the formula (A4-5), when a plurality of $A^{413}$ are present, they may be the same or different, when a plurality of $A^{423}$ are present, they may be the same or different, $Z^{413}$ and $Z^{423}$ each independently represent $—OCH_2—$, $—CH_2O—$, $—CH_2CH_2—$, or a single bond, when a plurality of $Z^{413}$ are present, they may be the same or different, when a plurality of $Z^{423}$ are present, they may be the same or different, m413 and m423 each independently represent 0, 1, or 2, and m413+m423 represents 1 or 2).

The compound represented by the general formula (IV) is particularly preferably a compound represented by general formula (IV-iv-1) to general formula (IV-iv-8) below.

[Chem. 62]

(IV-iv-1)

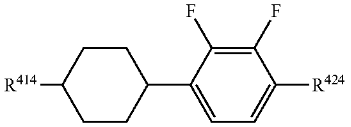

(IV-iv-2)

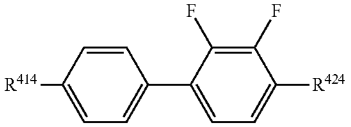

(IV-iv-3)

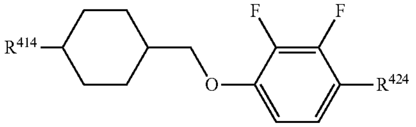

(IV-iv-4)

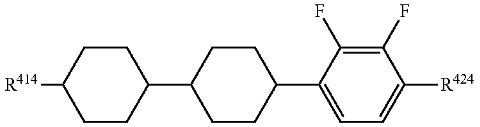

-continued

[Chem. 63]

(IV-iv-5)

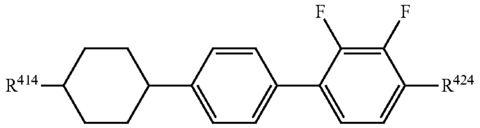

(IV-iv-6)

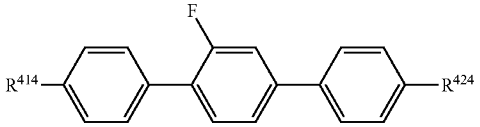

(IV-iv-7)

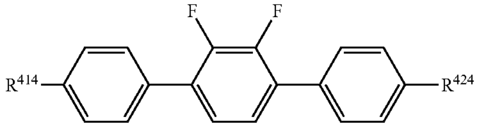

(IV-iv-8)

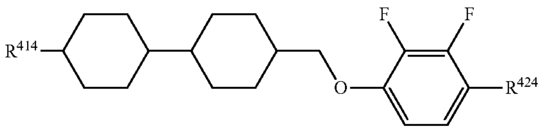

(In the formulae, $R^{414}$ and $R^{424}$ each independently represent an alkyl group having 1 to 5 carbon atoms, an alkoxy group having 1 to 4 carbon atoms, or an alkenyl group having 2 to 5 carbon atoms.)

In order to improve storage stability, a stabilizer can be added to the liquid crystal composition containing the compound (including more specific concepts) represented by the general formula (I). Usable examples of the stabilizer include hydroquinones, hydroquinone monoalkyl ethers, tert-butylcatechols, pyrogallols, thiophenols, nitro compounds, β-naphthylamines, β-naphthols, nitroso compounds, and the like. When the stabilizer is used, the adding amount relative to 100 parts by mass of the liquid crystal composition is preferably within a range of 0.005 parts by mass to 1 part by mass, more preferably 0.02 parts by mass to 0.8 parts by mass, and still more preferably 0.03 parts by mass to 0.5 parts by mass. In addition, one stabilizer may be used or two or more stabilizers may be used. The stabilizer is, for example, a compound represented by general formula (X1) below.

[Chem. 64]

(X1)

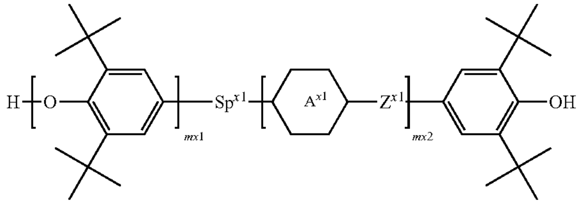

In the formula, $Sp^{x1}$ represents an alkylene group having 1 to 20 carbon atoms, in which one $—CH_2—$ or nonadjacent two or more $—CH_2—$ may be each independently substituted by —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, or a single bond, $A^{x1}$ represents a group selected from formula (Ax1-1) to formula (Ax1-8) below,

[Chem. 65]

(Ax1-1)

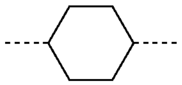

(Ax1-2)

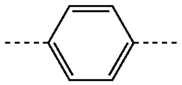

(Ax1-3)

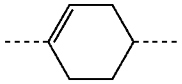

(Ax1-4)

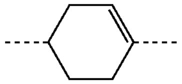

(Ax1-5)

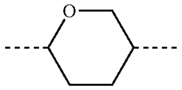

(Ax1-6)

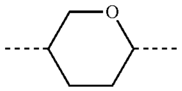

(Ax1-7)

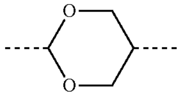

(Ax1-8)

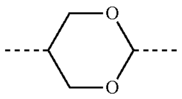

(in the formulae, a broken line represents a bond position), when a plurality of $A^{x1}$ are present, they may be the same or different, $Z^{x1}$ represents —O—, —S—, $—OCH_2—$, $—CH_2O—$, $—CH_2CH_2—$, —CO—, —COO—, —COO—, —CO—S—, —S—CO—, —O—CO—O—, —CO—NH—, —NH—CO—, —OCO—NH—, —NH—COO—, —NH—CO—NH—, NH O—, —O—NH—, $—SCH_2—$, $—CH_2S—$, $—CF_2O—$, $—OCF_2—$, $—CF_2S—$, $—SCF_2—$, —CH═CH—COO—, —CH═CH—OCO—, —COO—CH═CH—, —OCO—CH═CH—, $—COO—CH_2CH_2—$, $—COO—CH_2CH_2—$, $—CH_2CH_2—COO—$, $—CH_2CH_2—OCO—$, $—COO—CH_2—$, $—COO—CH_2—$, $—CH_2—COO—$, $—CH_2—OCO—$, —CH═CH—, —N═N—, —CH═N—, —N═CH—, —CH═N—N═CH—, —CF═CF—, —C≡C—, or a single bond, when a plurality of $Z^{X1}$ are present, they may be the same or different, mx1 represents 0 or 1, and mx2 represents an integer of 0 to 4).

From the viewpoint of voltage retention rate and compatibility with the liquid crystal composition, the compound represented by the general formula (X1) is preferably a compound represented by general formula (X1-i) below.

[Chem. 66]

(X1-i)

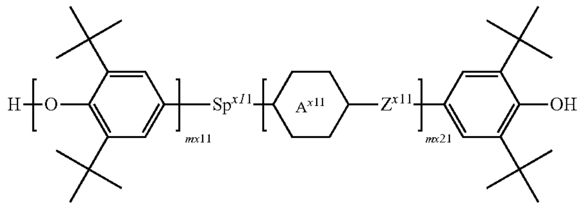

In the formula, $Sp^{x11}$ represents an alkylene group having 1 to 20 carbon atoms, in which one $—CH_2—$ or nonadjacent two or more $—CH_2—$ may be each independently substituted by —O—, —COO—, or —OCO—, or a single bond, $A^{x11}$ represents a group selected from formula (Ax11-1) and formula (Ax11-2) below,

[Chem. 67]

(Ax11-1)

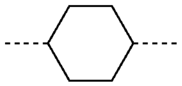

(Ax11-2)

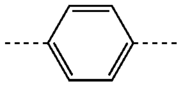

(in the formulae, a broken line represents a bond position), when a plurality of Ax11 are present, they may be the same or different, $Z^{x11}$ represents —COO—, —OCO—, $—COO—CH_2CH_2—$, $—CH_2CH_2—COO—$, or a single bond, when a plurality of $Z^{X11}$ are present, they may be the same or different, mx11 represents 0 or 1, and mx21 represents 0 or 1).

The compound represented by the general formula (X1) is particularly preferably a compound represented by general formula (X1-ii-1) to general formula (X1-ii-4) below.

[Chem. 68]

(X1-ii-1)

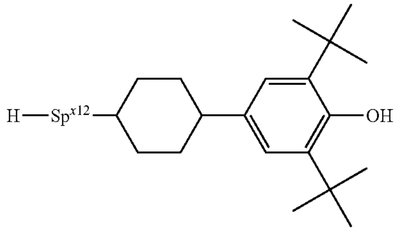

(X1-ii-2)

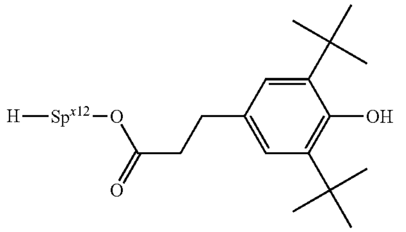

(X1-ii-3)

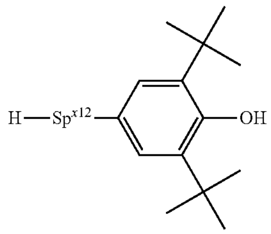

(X1-ii-4)

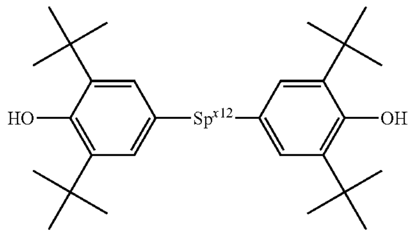

(In the formulae, $Sp^{x12}$ represents an alkylene group having 1 to 20 carbon atoms or a single bond.)

Other examples of the stabilizer include a compound represented by general formula (X2) below.

[Chem. 69]

(X2)

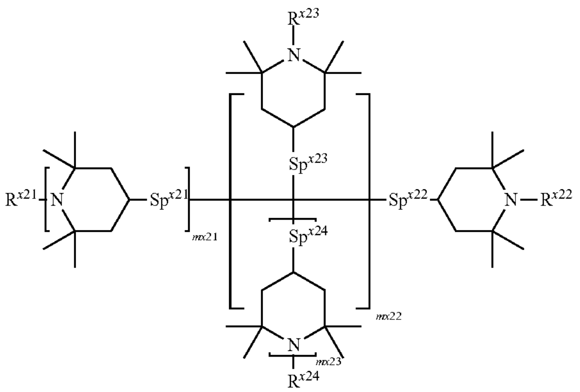

(In the formula, $R^{x21}$, $R^{x22}$, $R^{x23}$, and $R^{x24}$ each independently represent a hydrogen atom, an oxygen atom, a hydroxyl group, an alkyl group having 1 to 20 carbon atoms, or an alkoxy group having 1 to 20 carbon atoms, $Sp^{x21}$, $Sp^{x22}$, $Sp^{x23}$, and $Sp^{x24}$ each independently represent a spacer group or a single bond, mx21 represents 0 or 1, mx22 represents 0 or 1, and mx23 represents 0 or 1).

From the viewpoint of voltage retention rate and compatibility with the liquid crystal composition, the compound represented by the general formula (X2) is preferably a compound represented by general formula (X2-i) below.

[Chem. 70]

(X2-i)

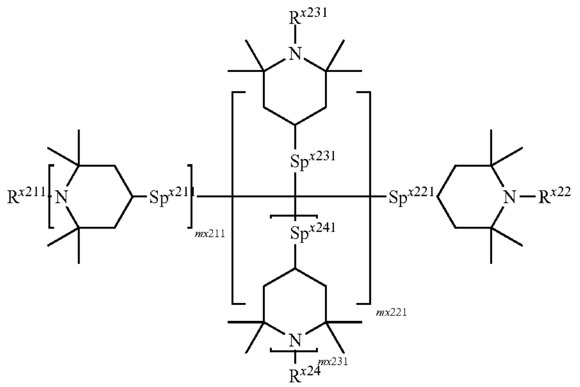

(In the formula, $R^{x211}$, $R^{x221}$, $R^{x231}$, and $R^{x241}$ each independently represent a hydrogen atom, an oxygen atom, a hydroxyl group, an alkyl group having 1 to 10 carbon atoms, or an alkoxy group having 1 to 10 carbon atoms, $Sp^{x211}$, $Sp^{x221}$, $Sp^{x231}$, and $Sp^{x241}$ each independently represent a linear or branched alkylene group having 1 to 20 carbon atoms, in which any hydrogen atom present in the group may be substituted by a fluorine atom, and one $-CH_2-$ or nonadjacent two or more $-CH_2-$ may be each independently substituted by —O—, —S—, —CO—, —COO—, —OCO—, —CO—S—, —S—CO—, —O—CO—O—, —CO—

NH—, —NH—CO—, —CH═CH—, —CF═CF—, or —C≡C—, or a single bond, mx211 represents 0 or 1, mx221 represents 0 or 1, and mx231 represents 0 or 1).

The compound represented by the general formula (X2) is more preferably a compound represented by general formula (X2-ii) below.

[Chem. 71]

(X2-ii)

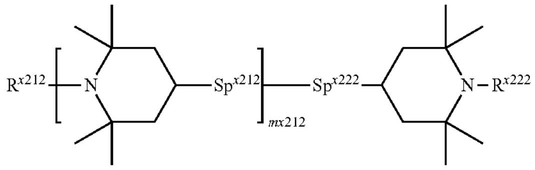

(In the formula, $R^{x212}$ and $R^{x222}$ each independently represent a hydrogen atom, an alkyl group having 1 to 10 carbon atoms, or an alkoxy group having 1 to 10 carbon atoms, $Sp^{x212}$ and $Sp^{x222}$ each independently represent a linear alkylene group having 1 to 10 carbon atoms, in which one $—CH_2—$ or nonadjacent two or more $—CH_2—$ may be each independently substituted by —O—, —COO—, or —OCO—, or a single bond, and mx212 represents 0 or 1).

The compound represented by the general formula (X2) is particularly preferably a compound represented by general formula (X2-iii) below.

[Chem. 72]

(X2-iii)

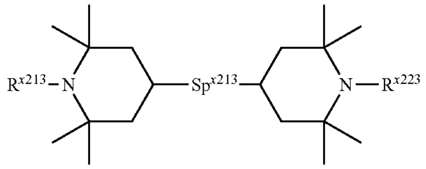

(In the formula, $R^{x213}$ and $R^{x223}$ each independently represent a hydrogen atom, an alkyl group having 1 to 10 carbon atoms, or an alkoxy group having 1 to 10 carbon atoms, and $Sp^{x213}$ represents a linear alkylene group having 1 to 10 carbon atoms, in which one $—CH_2—$ or nonadjacent two or more $—CH_2—$ may be each independently substituted by —COO— or —COO—).

EXAMPLES

The present invention further described by giving examples bellow, but the present invention is not limited to these examples. In addition, "%" in compositions of examples and comparative examples below represents "% by mass".

(Example 1) Production of Compound Represented by Formula (I-1)

[Chem. 73]

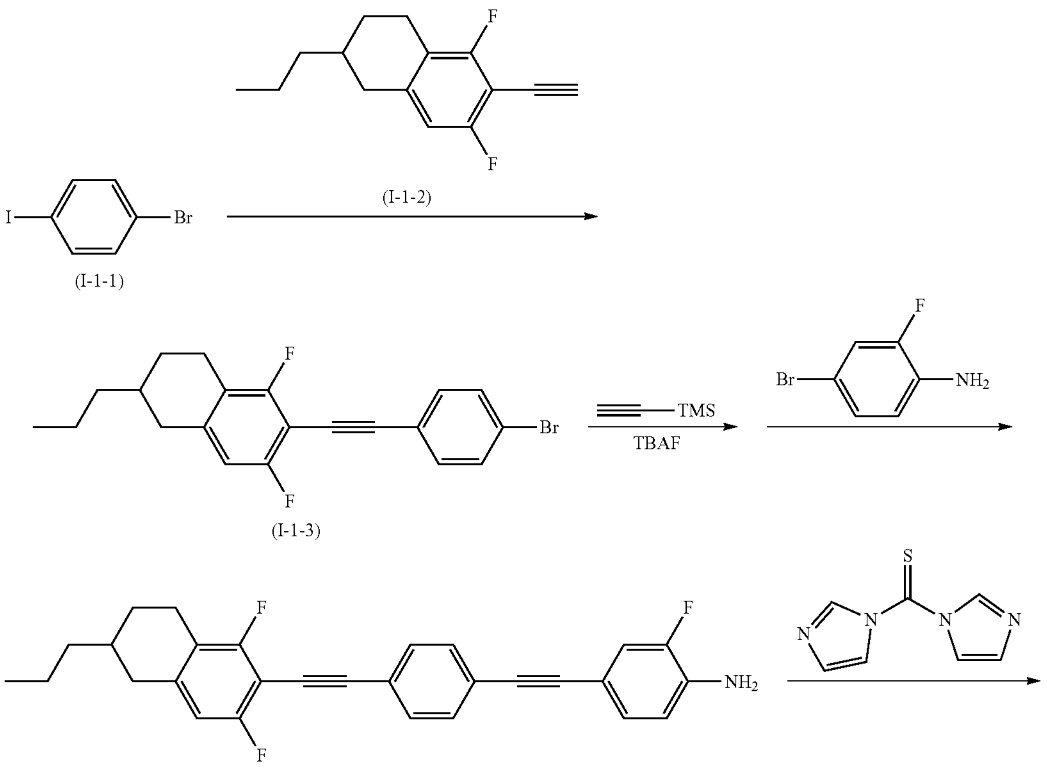

-continued

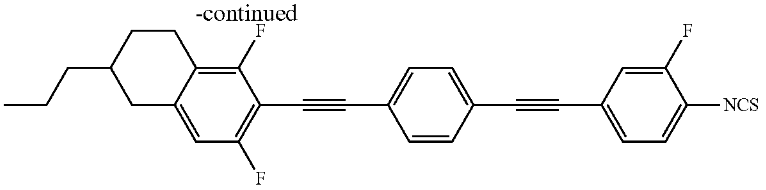

(I-1)

In a nitrogen atmosphere, into a reactor added were 10.0 g of a compound represented by formula (I-1-1), 0.3 g of copper(I) iodide, 0.5 g of bis(triphenylphosphine) palladium (II) dichloride, 25 mL of triethylamine, and 50 mL of tetrahydrofuran. A solution prepared by dissolving 9.9 g of a compound represented by formula (I-1-2) in 50 mL of tetrahydrofuran was added dropwise under stirring at room temperature, and then stirred for 1 hour at room temperature. Then, 10 mass % hydrochloric acid was poured into the reaction solution, followed by extraction with toluene. An organic layer was washed with saturated saline and then purified by column chromatography (silica gel, toluene) and recrystallization (toluene/hexane), producing 9.0 g of a compound represented by formula (I-1-3).

In a nitrogen atmosphere, into a reactor added were 9.0 g of the compound represented by the formula (I-1-3), 0.2 g of copper(I) iodide, 0.5 g of tetrakis(triphenylphosphine)palladium, 36 mL of triethylamine, and 18 mL of N,N-dimethylformamide. A solution prepared by dissolving 4.5 g of trimethylsilyl acetylene in 18 mL of N,N-dimethylformamide was added dropwise under heating at 75° C., and then stirred for 2 hours at 75° C. Then, 10 mass % hydrochloric acid was poured into the reaction solution, followed by extraction with toluene. An organic layer was washed with saturated saline and then subjected to column chromatography (silica gel, toluene) and recrystallization (toluene/hexane). Further, 3 g of potassium carbonate was added to 12 g of the resultant compound, and the resultant mixture was dissolved in 100 mL of methanol and then reacted at 40° C. for 2 hours. The reaction solution was extracted with toluene, and an organic layer was washed with saturated saline and then subjected to column chromatography (silica gel, toluene) and recrystallization (toluene/hexane). Then, in a nitrogen atmosphere, into a reactor added were 10.5 g of the resultant compound, 3.7 g of 4-bromo-2-fluoroaniline, 0.25 g of copper(I) iodide, 0.5 g of tetrakis(triphenylphosphine)palladium, 25 mL of triethylamine, and 80 mL of tetrahydrofuran. The reactor was heated to 80° C., and the reaction solution was further stirred for 3 hours. After the completion of reaction, an aqueous saturated ammonium chloride solution was poured into the reaction solution, and the solution was extracted with ethyl acetate. An organic layer was washed with saturated saline and then recrystallized with toluene, producing 9.3 g of a compound represented by formula (I-1-4). In a reactor, 9.3 g of the compound represented by the formula (I-1-4), 40 mL of dichloromethane, and 7 g of 1,1-thiocarbonyl diimidazole were added and heated under reflux for 2 hours. After the completion of reaction, an organic layer was washed with saturated saline and then purified by column chromatography (silica gel, dichloromethane) and recrystallization (toluene/hexane), producing 6.5 g of a compound represented by formula (I-1).

Cr 124 N

MS (E1): m/z=485

(Example 2) Production of Compound Represented by Formula (I-2)

[Chem. 74]

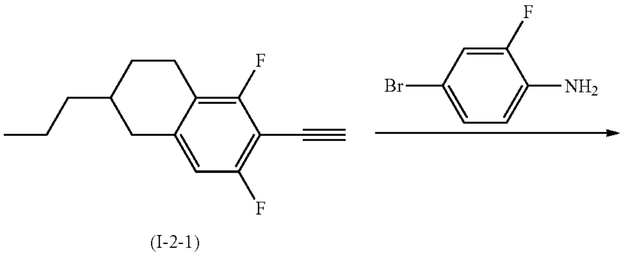

(I-2-1)

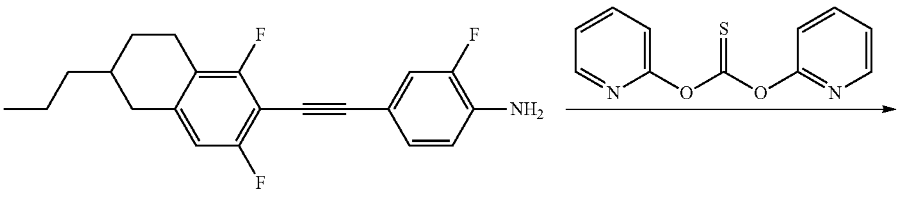

(I-2-2)

-continued

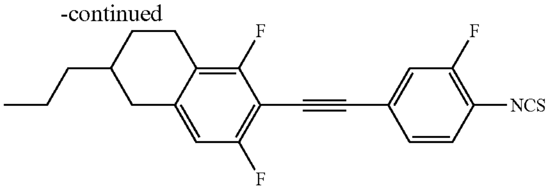

(I-2)

In a nitrogen atmosphere, into a reactor added were 10.0 g of 4-bromo-2-fluoroaniline, 0.4 g of copper(I) iodide, 0.5 g of tetrakis(triphenylphosphine)palladium, 35 mL of triethylamine, and 50 mL of tetrahydrofuran. A solution prepared by dissolving 12.3 g of a compound represented by formula (I-2-1) in 50 mL of tetrahydrofuran was added dropwise under stirring at room temperature, and then stirred for 1 hour at room temperature. Then, an aqueous saturated ammonium chloride solution was poured into the reaction solution, followed by extraction with toluene. An organic layer was washed with saturated saline and then purified by recrystallization with toluene, producing 14.5 g of a compound represented by formula (I-2-2).

Next, in a nitrogen atmosphere, into a reactor added were 14.5 g of the compound represented by the formula (I-2-2), 40 ml g of dichloromethane, and 9 g of 1,1-thiocarbonyl diimidazole, and the resultant mixture was heated under reflux for 2 hours. After the completion of reaction, an organic layer was washed with saturated saline and then purified by column chromatography (silica gel, dichloromethane) and recrystallization (toluene/hexane), producing 11.5 g of a compound represented by formula (I-2).

Cr 108 N 153 Iso

MS (EI): m/z=385

(Example 3) Production of Compound Represented by Formula (I-3)

[Chem. 75]

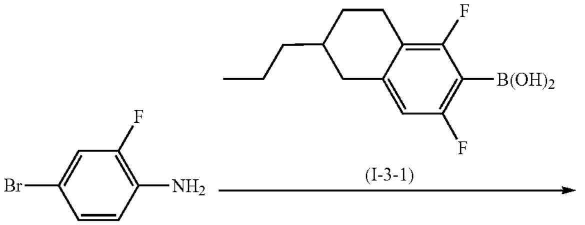

(I-3-1)

-continued

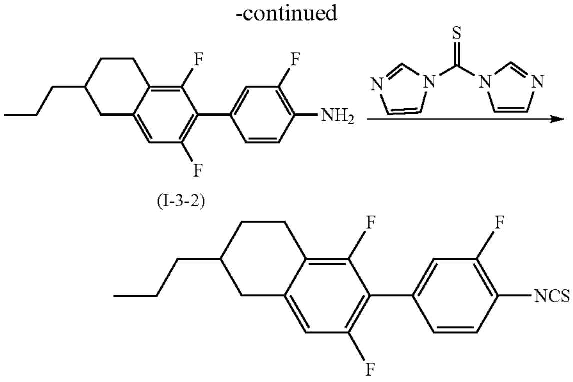

(I-3-2)

(I-3)

In a nitrogen atmosphere, into a reactor added were 10.0 g of a compound represented by formula (I-3-1), 6.8 g of 4-bromo-2-fluoroaniline, 340 mg of tetrakis(triphenylphosphine)palladium, 8.5 g of potassium carbonate, 75 mL of tetrahydrofuran, and 10 mL of water, and the reactor was heated to 70° C. After the completion of reaction, an aqueous saturated ammonium chloride solution was poured into the reaction solution, followed by extraction with ethyl acetate. An organic layer was washed with saturated saline and then recrystallized with toluene, producing 10.5 g of a compound represented by formula (I-3-2).

Next, in a nitrogen atmosphere, into a reactor added were 10.5 g of the compound represented by the formula (I-3-2), 40 ml of dichloromethane, and 6 g of 1,1-thiocarbonyl diimidazole, and the resultant mixture was heated under reflux for 2 hours. After the completion of reaction, an organic layer was washed with saturated saline and then purified by column chromatography (silica gel, dichloromethane) and recrystallization (toluene/hexane), producing 8.5 g of a compound represented by formula (I-3).

MS (EI): m/z=361

(Example 4) Production of Compound Represented by Formula (I-4)

[Chem. 76]

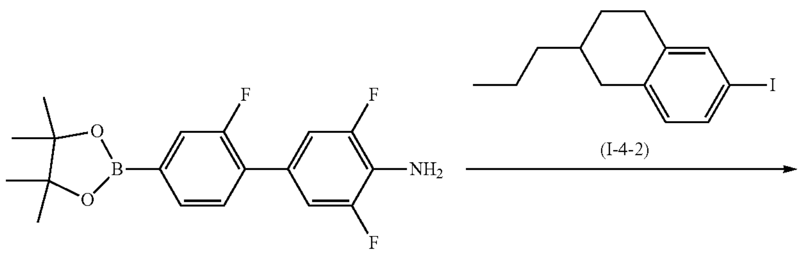

(I-4-2)

(I-4-1)

-continued

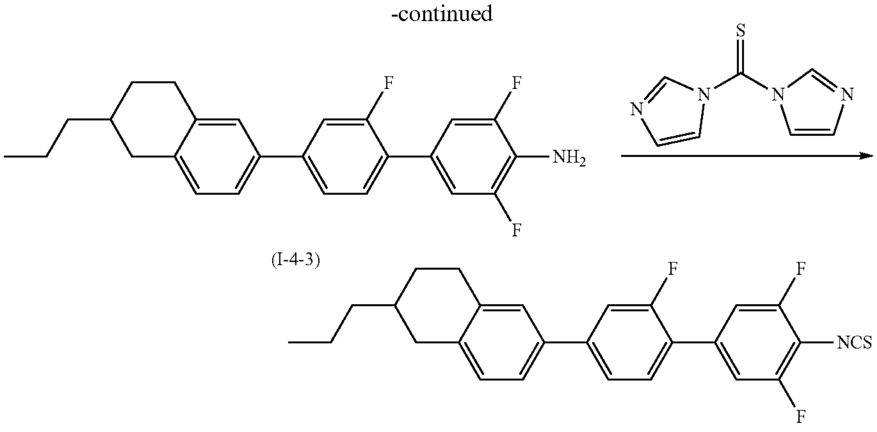

(I-4-3)

(I-4)

In a nitrogen atmosphere, into a reactor added were 10.0 g of a compound represented by formula (I-4-1), 8.6 g of a compound represented by formula (I-4-2), 320 mg of tetrakis(triphenylphosphine)palladium, 6 g of potassium carbonate, 75 mL of tetrahydrofuran, and 10 mL of water, and the reactor was heated to 70° C. After the completion of reaction, saturated ammonium chloride was poured into the reaction solution, followed by extraction with ethyl acetate. An organic layer was washed with saturated saline and then recrystallized with toluene, producing 8.5 g of a compound represented by formula (I-4-3).

Next, in a nitrogen atmosphere, into a reactor added were 8.5 g of the compound represented by the formula (I-4-3), 40 ml of dichloromethane, and 4 g of 1,1-thiocarbonyl diimidazole, and the resultant mixture was heated under reflux for 2 hours. After the completion of reaction, an organic layer was washed with saturated saline and then purified by column chromatography (silica gel, dichloromethane) and recrystallization (toluene/hexane), producing 7.0 g of a compound represented by formula (I-4).

MS (EI): m/z=437

(Example 5) Production of Compound Represented by Formula (I-5)

[Chem. 77]

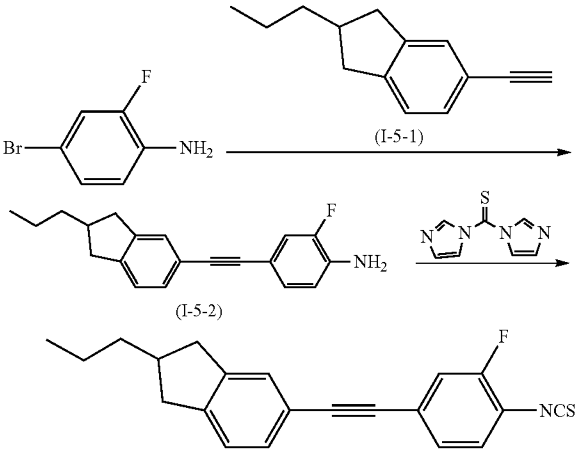

(I-5-1)

(I-5-2)

(I-5)

A compound represented by formula (I-5) was produced by the same method as in Example 2 except that the compound represented by the formula (I-2-1) was replaced by a compound represented by formula (I-5-1).

MS (EI): m/z=335

(Example 6) Production of Compound Represented by Formula (I-6)

[Chem. 78]

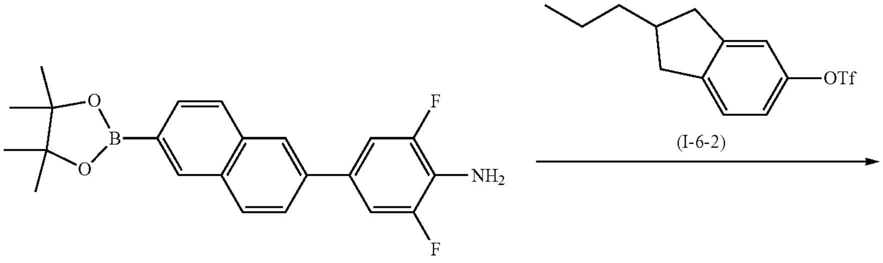

(I-6-2)

(I-6-1)

-continued

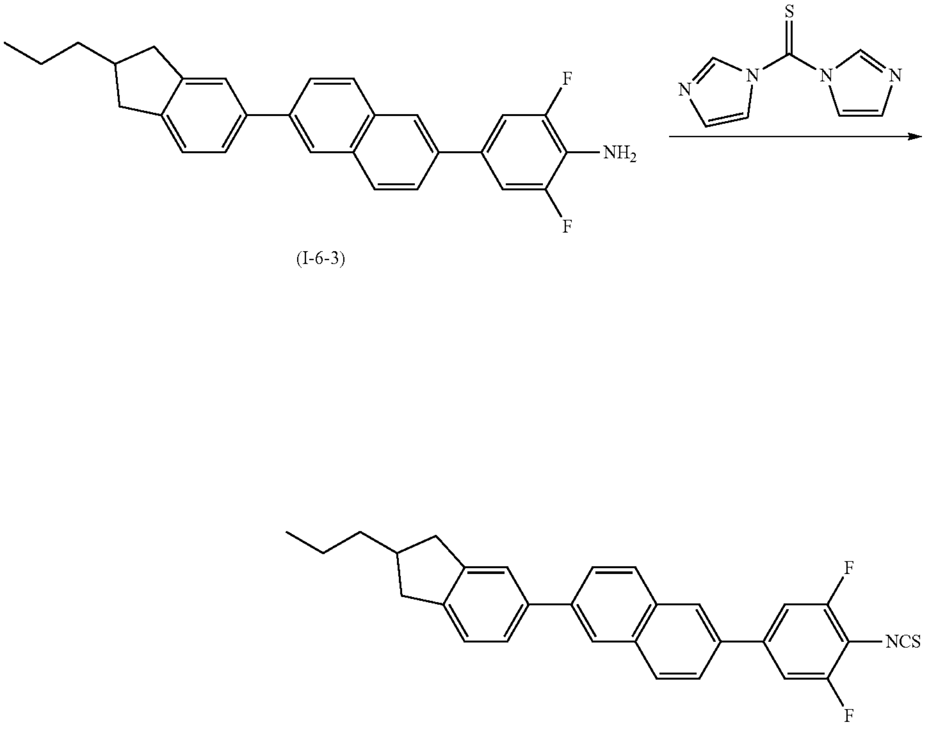

(I-6-3)

(I-6)

In a nitrogen atmosphere, into a reactor added were 10.0 g of a compound represented by formula (I-6-1), 8.4 g of a compound represented by formula (I-6-2), 300 mg of tetrakis(triphenylphosphine)palladium, 5.5 g of potassium carbonate, 75 mL of tetrahydrofuran, and 10 mL of water, and the reactor was heated to 70° C. After the completion of reaction, an aqueous saturated ammonium chloride solution was poured into the reaction solution, followed by extraction with ethyl acetate. An organic layer was washed with saturated saline and then recrystallized with toluene, producing 8.7 g of a compound represented by formula (I-6-3).

Next, in a nitrogen atmosphere, into a reactor added were 8.7 g of the compound represented by the formula (I-6-3), 40 ml of dichloromethane, and 3.8 g of 1,1-thiocarbonyl diimidazole, and the resultant mixture was heated under reflux for 2 hours. After the completion of reaction, an organic layer was washed with saturated saline and then purified by column chromatography (silica gel, dichloromethane) and recrystallization (toluene/hexane), producing 8.2 g of a compound represented by formula (I-6).

MS (EI): m/z=455

(Example 7) Production of Compound Represented by Formula (I-7)

[Chem. 79]

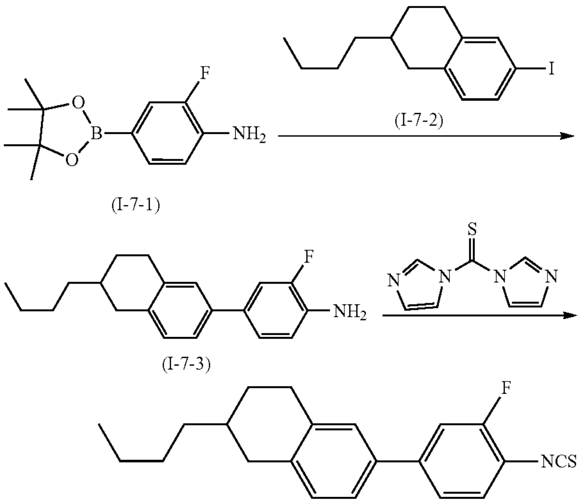

(I-7-2)

(I-7-1)

(I-7-3)

(I-7)

A compound represented by formula (I-7) was produced by the same method as in Example 4 except that in Example 4, the compounds represented by the formula (I-4-1) and the formula (I-4-2) were replaced by compounds represented by formula (I-7-1) and formula (I-7-2).

MS (EI): m/z=339

(Example 8) Production of Compound Represented by Formula (I-8)

[Chem. 80]

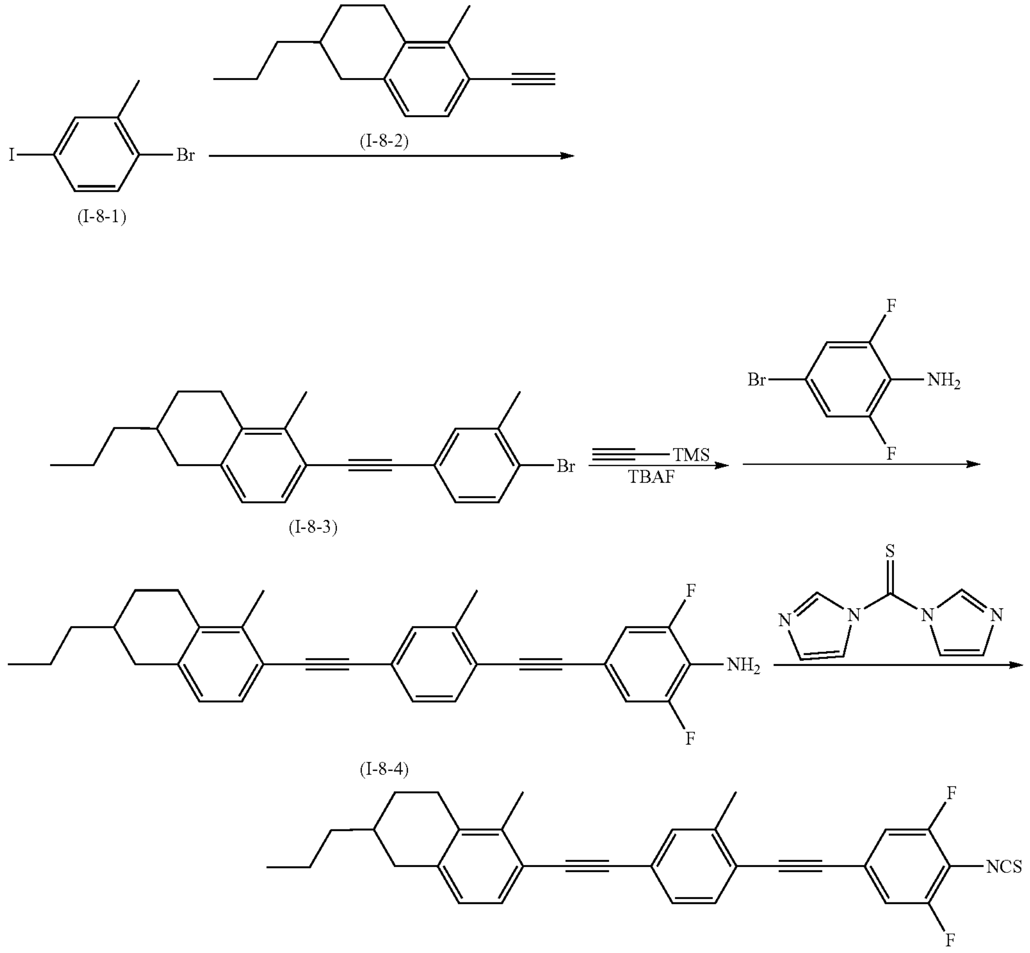

(I-8-1)

(I-8-2)

(I-8-3)

(I-8-4)

(I-8)

A compound represented by formula (I-8) was produced by the same method as in Example 1 except that in Example 1, the compounds represented by the formula (I-1-1) and the formula (I-1-2) were replaced by compounds represented by formula (I-8-1) and formula (I-8-2).

MS (EI): m/z=495

(Example 9) Production of Compound Represented by Formula (I-9)

[Chem. 81]

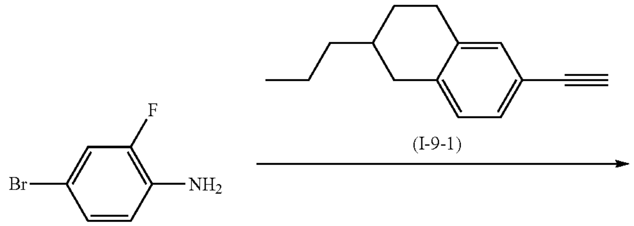

(I-9-1)

-continued
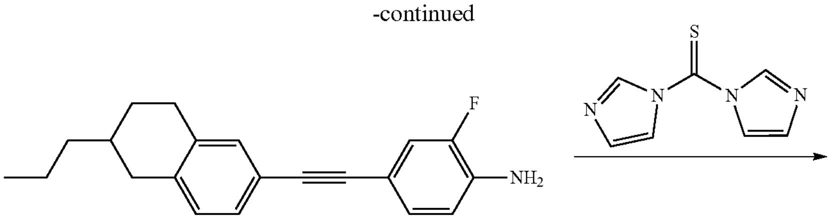
(I-9-2)
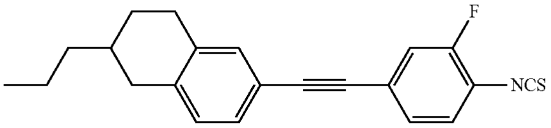
(I-9)
A compound represented by formula (I-9) was produced by the same method as in Example 2 except that the compound represented by the formula (I-2-1) was replaced by a compounds represented by formula (I-9-1).
MS (EI): m/z=349
(Example 10) Production of Compound Represented by Formula (I-10)
[Chem. 82]
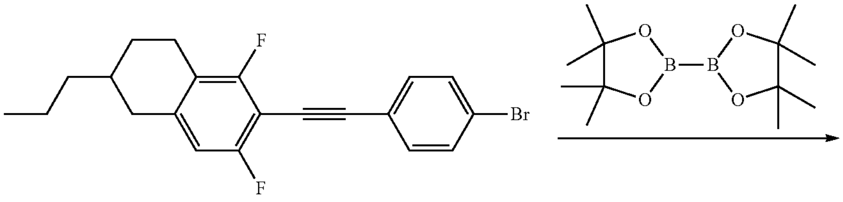
(I-10-1)
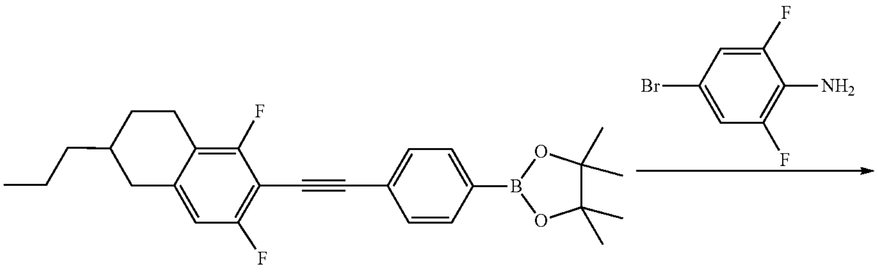
(I-10-2)
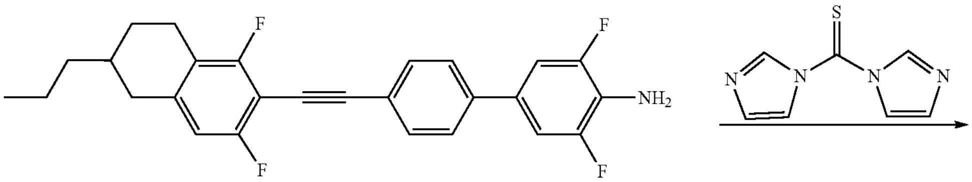
(I-10-3)
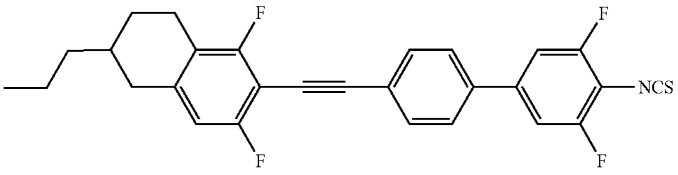
(I-10)

In a nitrogen atmosphere, into a reactor added were 9 g of a compound represented by formula (I-10-1), 7 g of bis (pinacolato) diborane, 7 g of potassium acetate, 500 mg of bis(diphenylphosphino)-ferrocene palladium, and 100 ml of N,N-dimethylformamide, and the reactor was heated to 80° C. After the completion of reaction, saturated ammonium chloride was poured into the reaction solution, followed by extraction with ethyl acetate. An organic layer was washed with saturated saline and then recrystallized with hexane, producing 6 g of a compound represented by formula (I-10-2).

Next, in a nitrogen atmosphere, into a reactor added were 6 g of the compound represented by the formula (I-10-2), 3 g of 4-bromo-2,6-difluoroaniline, 40 mg of tetrakis(triphenylphosphine)palladium, 5 g of potassium carbonate, 75 mL of tetrahydrofuran, and 10 mL of water, and the resultant mixture was heated to 70° C. After the completion of reaction, an aqueous saturated ammonium chloride solution was poured into the reaction solution, followed by extraction with ethyl acetate. An organic layer was washed with saturated saline and then purified by column chromatography (silica gel, dichloromethane) and recrystallization (toluene/tetrahydrofuran), producing 3.5 g of a compound represented by formula (I-10-3).

Next, in a nitrogen atmosphere, into a reactor added were 3.5 g of the compound represented by the formula (I-10-3), 30 ml of dichloromethane, and 7 g of 1,1-thiocarbonyl diimidazole, and the resultant mixture was heated under reflux for 2 hours. After the completion of reaction, an organic layer was washed with saturated saline and then purified by column chromatography (silica gel, dichloromethane) and recrystallization (toluene/tetrahydrofuran), producing 2.5 g of a compound represented by formula (I-10).

Cr 122 Sm 130 N 285 Iso

MS (EI): m/z=479

(Example 11) Production of Compound Represented by Formula (I-11)

[Chem. 83]

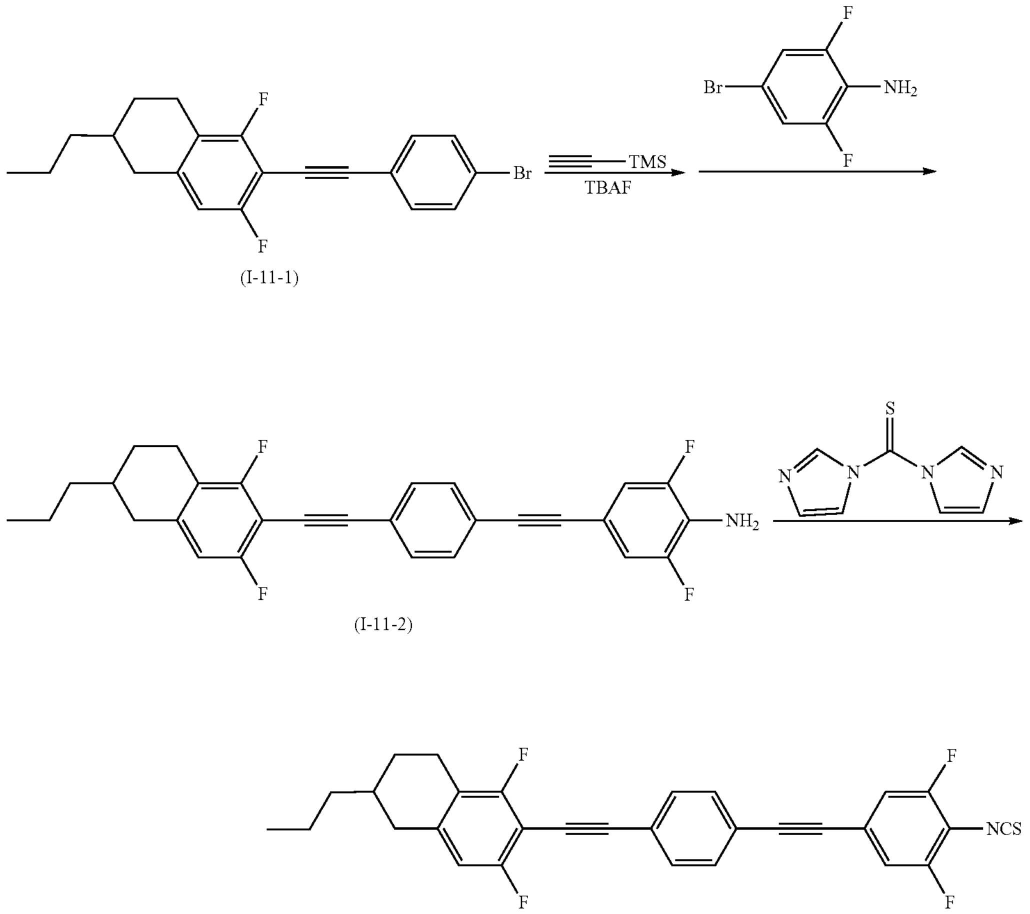

(I-11-1)

(I-11-2)

(I-11)

A compound represented by formula (I-11) was produced by the same method as in Example 1 except that 4-bromo-2-fluoroaniline was replaced by 4-bromo-2,6-difluoroaniline.

MS (EI): m/z=503

Preparation and Evaluation of Liquid Crystal Composition

A mother liquid crystal (LC-1) showing physical property values below was prepared. All the values are measured values.

$T_{n-i}$ (nematic phase-isotropic liquid phase transition temperature): 74.0° C.

$\Delta\varepsilon$ (dielectric anisotropy at 25° C., 1 kHz): 5.11

$\Delta n$ (refractive index anisotropy at 25° C.): 0.141

$\gamma_1$ (rotational viscosity coefficient at 25° C.): 107

A liquid crystal composition was prepared by adding 0 parts by mass, 5 parts by mass, and 10 parts by mass of the compound (I-1) produced in an example relative to 100 parts by mass of the mother liquid crystal (LC-1), and $\Delta n$, $\Delta\varepsilon$, and $T_{n-i}$ of each of the liquid crystal compositions were measured. In addition, $\Delta n$, $\Delta\varepsilon$, and $T_{n-i}$ of 100 parts of the compound (I-1), that is, the compound (I-1), were determined from extrapolation values using a least-squares method. Similarly, $\Delta n$, $\Delta\varepsilon$, and $T_{n-i}$ of the compounds (I-2), (I-4) to (I-6), and (I-9), and compounds represented by formula (C-1) to (C-4) described in patent literature were determined from extrapolation values.

[Chem. 84]

(C-1)

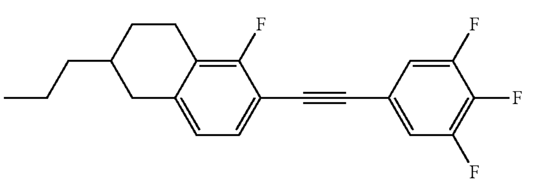

(C-2)

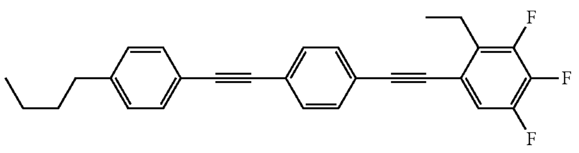

(C-3)

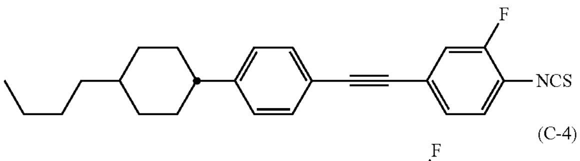

(C-4)

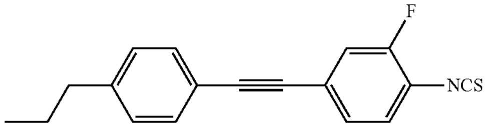

Table 1 shows the results. Comparison between Examples 12 to 18 and Comparative Examples 1 to 4 indicates that $T_{n-i}$, $\Delta n$, and $\Delta\varepsilon$ can be effectively increased by adding a compound of the present invention to a liquid crystal composition.

TABLE 1

| | Compound | Δn | Δε | $T_{n-i}$ |
|---|---|---|---|---|
| Comparative Example 1 | (C-1) | 0.248 | 13.7 | 74.0 |
| Comparative Example 2 | (C-2) | 0.326 | 11.3 | 108.0 |
| Comparative Example 3 | (C-3) | 0.325 | 13.0 | 195.0 |
| Comparative Example 4 | (C-4) | 0.334 | 14.5 | 35.0 |
| Example 8 | (I-1) | 0.557 | 21.7 | >250.0 |
| Example 12 | (I-2) | 0.357 | 23.1 | 107.0 |
| Example 13 | (I-4) | 0.344 | 19.0 | >250.0 |
| Example 14 | (I-5) | 0.412 | 17.0 | 115.0 |
| Example 15 | (I-6) | 0.445 | 21.5 | 215.0 |
| Example 16 | (I-9) | 0.387 | 17.5 | 135.0 |
| Example 17 | (I-10) | 0.442 | 27.5 | 230.0 |
| Example 18 | (I-11) | 0.503 | 26.0 | 234.0 |

Example 19 and Comparative Example 5

Next, relative to 100 parts by mass of the mother liquid crystal (LC-1), a liquid crystal composition was prepared by adding 12 parts by mass of the compound (I-1) produced in Example 1, and a liquid crystal composition was prepared by adding 12 parts by mass of a compound represented by formula (C-5). The resultant liquid crystal compositions were stored for 1 week at each of room temperature (25° C.) and −10° C., and the presence of precipitation was visually determined.

Even when the liquid crystal composition prepared by adding the compound (I-1) was stored at −10° C. for 1 week, precipitation was not observed, and thus storage stability was excellent (Example 19).

On the other hand, when the liquid crystal composition prepared by adding the compound (C-5) was stored at −10° C., precipitation was observed 3 days later (Comparative Example 5).

[Chem. 85]

(C-5)

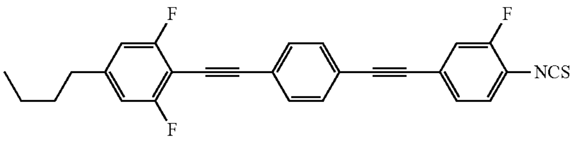

The invention claimed is:

1. A compound represented by general formula (I) below, (I)

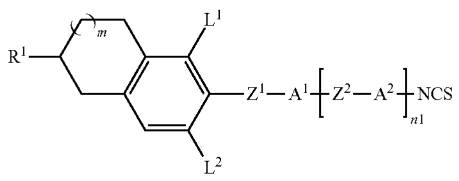

in the formula, $R^1$ represents a hydrogen atom, a linear alkyl group having 1 to 20 carbon atoms, or a branched or cyclic alkyl group having 3 to 20 carbon atoms, any hydrogen atom in the alkyl group may be substituted by a halogen atom, one or two or more —$CH_2$— in the alkyl group may be each independently substituted by —O—, —S—, —CO—, —CS—, —COO—, —OCO—, —CO—S—, —S—CO—, —O—CO—O—, —CO—NH—, —NH—CO—, —CH═CH—, —CF═CF—, or —C≡C—, but oxygen atoms are not directly bonded to each other, $A^1$ and $A^2$ each independently represent a hydrocarbon ring or hetero ring having 3 to 16 carbon atoms, which may be substituted, when a plurality of $A^2$ are present, they may be the same or different, $L^1$ and $L^2$ each independently represent a hydrogen atom, a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear alkyl group having 1 to 20 carbon atoms or a branched or cyclic alkyl group having 3 to 20 carbon atoms, in which one —$CH_2$— or two or more —$CH_2$— may be each independently substituted by —O—, —S—, —CO—, —CS—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, oxygen atoms are not directly bonded to each other, any hydrogen atom in the alkyl group may be substituted by a fluorine atom, $Z^1$ and $Z^2$ each independently represent a single bond, —CH═CH—, —CF≡CF—, —C≡C—, —COO—, —OCO—, —OCOO—, —$CH_2O$—, —$OCH_2$—, —$CF_2O$—, —$OCF_2$—, —CH═CHCOO—, —OCOCH═CH—, —CH═C($CH_3$)COO—, —OCOC($CH_3$)═CH—, —$CH_2$—CH($CH_3$)COO—, —OCOCH($CH_3$)—$CH_2$—, —$OCH_2CH_2O$—, —CH═N—N═CH—, —CH═N—, —N═CH—, —N═N—, or an alkylene group having 1 to 20 carbon atoms, one or two or more —$CH_2$— in the alkylene group may be each independently substituted by —O—, —COO—, or —OCO—, but oxygen atoms are not directly bonded to each other, when a plurality of $Z^2$ are present, they may be the same or different, m represents 0 or 1, and n1 represents an integer of 0 to 3.

2. The compound according to claim 1, wherein in the general formula (I), $A^1$ and $A^2$ each represent a group selected from the group consisting of:

(a) a 1,4-cyclyhexylene group, wherein one —$CH_2$— or two or more nonadjacent —$CH_2$— present in the group may be substituted by —O— or —S—;

(b) a 1,4-phenylene group, wherein one —CH═ or two or more nonadjacent —CH═ present in the group may be substituted by —N═;

(c) a 1,4-cyclohexenylene group, a bicyclo[2.2.2]octane-1,4-diyl group, a naphthalene-2,6-diyl group, a naphthalene-1,4-diyl group, a 1,2,3,4-tetrahydronaphthalene-2,6-diyl group, a 5,6,7,8-tetrahydronaphthalene-1,4-diyl group, a decahydronaphthalene-2,6-diyl group, an anthracene-2,6-diyl group, an anthracene-1,4-diyl group, an anthracene-9,10-diyl group, and a phenanthrene-2,7-diyl group, wherein a hydrogen atom present in each of these groups may be substituted by a fluorine atom or a chlorine atom, and one —CH═ or two or more —CH═ present in a naphthalene-2,6-diyl group, a naphthalene-1,4-diyl group, a 1,2,3,4-tetrahydronaphthalene-2,6-diyl group, a 5,6,7,8-tetrahydronaphthalene-1,4-diyl group, an anthracene-2,6-diyl group, an anthracene-1,4-diyl group, an anthracene-9,10-diyl group, or a phenanthrene-2,7-diyl group may be substituted by —N═; and (d) a thiophene-2,5-diyl group, a benzothiophene-2,5-diyl group, a benzothiophene-2,6-diyl group, a dibenzothiophene-3,7-diyl group, a dibenzothiophene-2,6-diyl group, and a thieno[3,2-b]thiophene-2,5-diyl group, wherein one —CH═ or two or more nonadjacent —CH═ present in each of these groups may be substituted by —N═, these groups may be unsubstituted or substituted by one or more substituents $L^3$, $L^3$ each independently represent a hydrogen atom, a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear alkyl group having 1 to 20 carbon atoms or a branched or cyclic alkyl group having 3 to 20 carbon atoms, in which one —$CH_2$— or two or more —$CH_2$— may be each independently may substituted by —O—, —S—, —CO—, —CS—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, oxygen atoms are not directly bonded to each other, and any hydrogen atom in the alkyl group may be substituted by a fluorine atom.

3. The compound according to claim 1, wherein the general formula (I) is represented by general formula (I-i) below, (I-i)

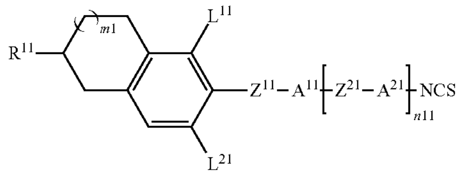

in the formula, $R^{11}$ represents a hydrogen atom or a linear or branched alkyl group having 1 to 20 carbon atoms, any hydrogen atom in the alkyl group may be substituted by a halogen atom, one or two or more —$CH_2$— in the alkyl group may be each independently substituted by —O—, —S—, —CH═CH—, —CF═CF—, or —C≡C—, $A^{11}$ and $A^{21}$ each independently represent a 1,4-phenylene group, a naphthalene-2,6-diyl group, a naphthalene-1,4-diyl group, a 5,6,7,8-tetrahydronaphthalene-1,4-diyl group, a phenanthrene-2,7-diyl group, a benzothiophene-2,5-diyl group, a benzothiophene-2,6-diyl group, a benzothiazole-2,5-diyl group, a benzothiazole-2,6-diyl group, a dibenzothiophene-3,7-diyl group, a dibenzothiophene-2,6-diyl group, or a thieno [3,2-b] thiophene-2,5-diyl group, when a plurality of $A^{21}$ are present, they may be the same or different, these groups may be unsubstituted or substituted by one or more substituents $L^{31}$, $L^{11}$ and $L^{21}$ each independently represent a hydrogen atom, a fluorine atom, a chlorine atom, or a linear alkyl group having 1 to 20 carbon atoms or a branched or cyclic alkyl group having 3 to 20 carbon atoms, any hydrogen atom in the alkyl group may be substituted by a fluorine atom, one $-CH_2-$ or two or more $-CH_2-$ in the alkyl group may be each independently substituted by $-O-$, $-S-$, $-CH{=}CH-$, $-CF{=}CF-$, or $-C{\equiv}C-$, $L^{31}$ each independently represent a fluorine atom, a chlorine atom, or a linear alkyl group having 1 to 20 carbon atoms or a branched or cyclic alkyl group having 3 to 20 carbon atoms, any hydrogen atom in the alkyl group may be substituted by a fluorine atom, one $-CH_2-$ or two or more $-CH_2-$ in the alkyl group may be each independently substituted by $-O-$, $-S-$, $-CH{=}CH-$, $-CF{=}CF-$, or $-C{\equiv}C-$, when a plurality of $L^{31}$ are present, they may be the same or different, $Z^{11}$ and $Z^{21}$ each independently represent $-OCH_2-$, $-CH_2O-$, $-CH_2CH_2-$, $-CF_2O-$, $-OCF_2-$, $-CH{=}CH-$, $-N{=}N-$, $-CH{=}N-$, $-N{=}CH-$, $-N{=}N-$, $-CH{=}N-N{=}CH-$, $-CF{=}CF-$, $-C{\equiv}C-$, or single bond, when a plurality of $Z^{21}$ are present, they may be the same or different, at least one of $Z^{11}$ and $Z^{21}$ present in the formula represents $-C{\equiv}C-$, m1 represents 0 or 1, and n11 represents an integer of 0 to 3.

4. The compound according to claim 1, wherein the general formula (I) is represented by general formula (I-ii) below, (I-ii)

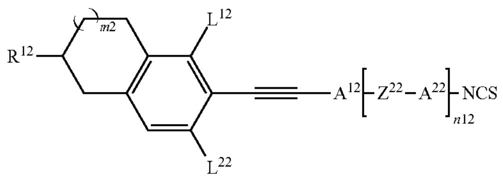

in the formula, $R^{12}$ represents a linear or branched alkyl group having 1 to 12 carbon atoms, any hydrogen atom in the alkyl group may be substituted by a fluorine atom, one or two or more $-CH_2-$ in the alkyl group may be each independently substituted by $-O-$, $-CH{=}CH-$, or $-C{\equiv}C-$, $A^{12}$ and $A^{22}$ each independently represent a group selected from formula (A-ii-1) to formula (A-ii-17) below, (A-ii-1)

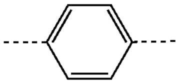

(A-ii-2)

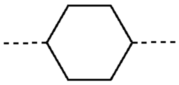

(A-ii-3)

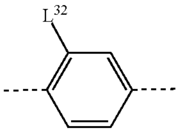

(A-ii-4)

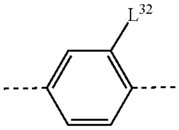

(A-ii-5)

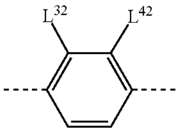

(A-ii-6)

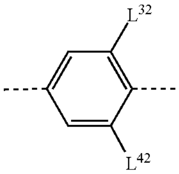

(A-ii-7)

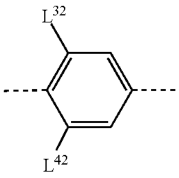

(A-ii-8)

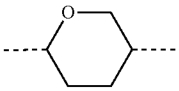

(A-ii-9)

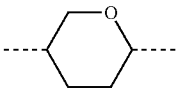

(A-ii-10)

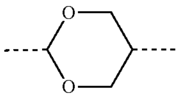

(A-ii-11)

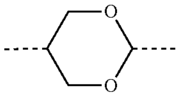

(A-ii-12)

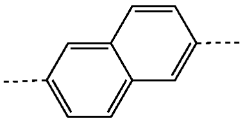

-continued (A-ii-13)

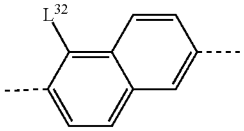

(A-ii-14)

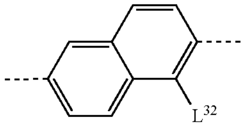

(A-ii-15)

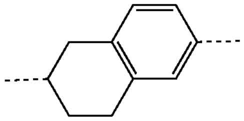

(A-ii-16)

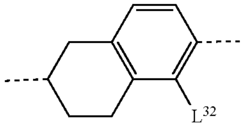

(A-ii-17)

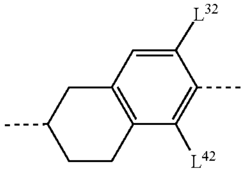

in the formulae, a broken line represents a bond position, and when a plurality of each of $L^{32}$ and $L^{42}$ are present, they may be the same or different, when a plurality of $A^{22}$ are present, they may be the same or different, $L^{12}$, $L^{22}$, $L^{32}$, and $L^{42}$ each independently represent a hydrogen atom, a fluorine atom, or a linear alkyl group having 1 to 10 carbon atoms or a branched or cyclic alkyl group having 3 to 10 carbon atoms, any hydrogen atom in the alkyl group may be substituted by a fluorine atom, $-CH_2-$ in the alkyl group may be substituted by $-O-$, $Z^{22}$ each independently represent $-CH{=}CH-$, $-N{=}N-$, $-CH{=}N-$, $-N{=}CH-$, $-N{=}N-$, $-CH{=}N-N{=}CH-$, $-CF{=}CF-$, $-C{\equiv}C-$, or single bond, when a plurality of $Z^{22}$ are present, they may be the same or different, m2 represents 0 or 1, and n12 represents an integer of 1 to 3.

5. A composition comprising the compound according to claim 1.

6. A liquid crystal composition comprising the compound according to claim 1.

7. The liquid crystal composition according to claim 6, wherein the refractive index anisotropy is 0.15 or more and 1.00 or less.

8. The liquid crystal composition according to claim 6, wherein the dielectric anisotropy is 2 or more and 60 or less.

9. The liquid crystal composition according to claim 6, wherein the dielectric anisotropy is −20 or more and 2 or less.

10. A high-frequency phase shifter, comprising the liquid crystal composition according to claim 6.

11. A phased array antenna, comprising the liquid crystal composition according to claim 6.

12. An image recognition device, comprising the liquid crystal composition according to claim 6.

13. A distance measuring device, comprising the liquid crystal composition according to claim 6.

14. A liquid crystal display device, comprising the liquid crystal composition according to claim 6.

15. A liquid crystal lens, comprising the liquid crystal composition according to claim 6.

16. A birefringent lens for stereoscopic image display, comprising the liquid crystal composition according to claim 6.

* * * * *